US012600742B2

(12) United States Patent
Kumar et al.

(10) Patent No.: US 12,600,742 B2
(45) Date of Patent: *Apr. 14, 2026

(54) MARKERS, CONJUGATES, COMPOSITIONS AND METHODS FOR HYPOXIA IMAGING, MAPPING, AND THERAPY

(71) Applicant: WWIKY BIOSCIENCES INC., Edmonton (CA)

(72) Inventors: Piyush Kumar, Edmonton (CA); Hassan Elsaidi, Edmonton (CA); Leonard Irving Wiebe, Edmonton (CA); Michael Weinfeld, Edmonton (CA)

(73) Assignee: WWIKY Biosciences Inc., Edmonton (CA)

(*) Notice: Subject to any disclaimer, the term of this patent is extended or adjusted under 35 U.S.C. 154(b) by 734 days.

This patent is subject to a terminal disclaimer.

(21) Appl. No.: 16/648,338

(22) PCT Filed: Sep. 19, 2018

(86) PCT No.: PCT/CA2018/051165

§ 371 (c)(1),
(2) Date: Mar. 18, 2020

(87) PCT Pub. No.: WO2019/056097

PCT Pub. Date: Mar. 28, 2019

(65) Prior Publication Data

US 2020/0216486 A1 Jul. 9, 2020

Related U.S. Application Data

(60) Provisional application No. 62/560,478, filed on Sep. 19, 2017.

(51) Int. Cl.

| | |
|---|---|
| ***C07H 15/26*** | (2006.01) |
| ***A61K 51/04*** | (2006.01) |
| ***C07D 253/08*** | (2006.01) |
| ***C07D 403/12*** | (2006.01) |
| ***C07D 405/14*** | (2006.01) |

(52) U.S. Cl.

CPC ......... *C07H 15/26* (2013.01); *A61K 51/0453* (2013.01); *A61K 51/0461* (2013.01); *A61K 51/0497* (2013.01); *C07D 253/08* (2013.01); *C07D 403/12* (2013.01); *C07D 405/14* (2013.01)

(58) Field of Classification Search

CPC .... C07H 15/26; C07D 245/08; C07D 403/12; C07D 405/14; C07D 405/04; A61K 51/0453; A61K 51/0461; A61K 51/0497

USPC .......................................................... 514/25

See application file for complete search history.

(56) References Cited

U.S. PATENT DOCUMENTS

2022/0249710 A1 8/2022 Kumar et al.

FOREIGN PATENT DOCUMENTS

| | | | | |
|---|---|---|---|---|
| CN | 101624392 A | * | 1/2010 | ........... C07D 403/06 |
| CN | 101652360 A | | 2/2010 | |
| CN | 101709060 A | | 5/2010 | |
| CN | 101921263 A | | 12/2010 | |
| WO | WO-0043004 A1 | | 7/2000 | |
| WO | WO 2004/026846 A1 | * | 4/2004 | ........... C07D 403/12 |
| WO | WO-2008124651 A2 | | 10/2008 | |

OTHER PUBLICATIONS

Brown, Cancer Research, 1999, 59, 5863-5870.*
Hou, Ph.D. Thesis, Nov. 2016, pp. 1-299.*
Wu et al, Contrast Media Mol Imaging, 2015, 10(6), 465-472.*
Wang et al., J. Immunol. 2007, 179(9), pp. 5958-5965.*
Suchy et al, Eur J Org Chem, 2011, 6532-6543.*
Kumar et al, J. Med. Chem., 2012, 55, 6033-6046.*
Bar et al., "Hypoxia Increases the Expression of Stem-Cell Markers and Promotes Clonogenicity in Giloblastoma Neurospheres," The American Journal of Pathology. 177(3):1491-1502 (2010).
Bencokova et al., "ATM Activation and Signaling Under Hypoxic Conditions," Molecular and Cellular Biology. 29(2):526-537 (2009).
Bennewith et al., "Targeting Hypoxic Tumour Cells to OVercome Metastasis," BMC Cancer. 11:504 (2011).
Bindra et al., "Regulation of DNA Repair in Hypoxic Cancer Cells," Cancer Metastasis Reviews. 26(2):249-260 (2007).
Birner et al., "Vascular Patterns in Glioblastoma Influence Clinical Outcome and Associate With Variable Expression of Angiogenic Proteins: Evidence for Distinct Angiogenic Subtypes," Brain Pathology. 13(2):133-143 (2003).

(Continued)

*Primary Examiner* — Ganapathy Krishnan
(74) *Attorney, Agent, or Firm* — Clark & Elbing LLP

(57) ABSTRACT

Described herein are markers, conjugates, compositions and methods for hypoxia imaging, mapping, and therapy. A compound comprising bio-reductively activated (BA) arm, linker arm and a mapping click wherein BA contains one for more of substituted or unsubstituted 2/4/5-substituted nitroimidazoles, or substituted benzotriazene-1,4-dioxides, or substituted 1,2,3/1,2,4-triazoles, or substituted 1,4-benzoquinones, or a combination of two homo-or hetero BA moieties, wherein linker arm contains C1-16 alkane, alkene, alkyne, alicyclic or aromatic linkers with or without hetero atoms as in ethers, amine, esters, acid, amides, 5 and 6 membered sugar sings with the substitution as described above, both monosaccharides and disaccharides, wherein mapping click contains one of substituted or unsubstituted —N3-, CN, SCN, substituted alkynes for click chemistry. Said compound undergoes in situ click reaction after its distribution in cells or tissues to link to a reporting group which may be unchelated or chelated with a metal-radioactive or non-radioactive-, or a radiohalogen for PET/SPECT, or a dye for fluorescent/optical reporting group, thus accomplishing hypoxia imaging.

5 Claims, 11 Drawing Sheets

(56) References Cited

OTHER PUBLICATIONS

Blazek et al., "Daoy Medulloblastoma Cells that Express CD133 Are Radioresistant Relative to CD133-Cells, and the CD133+ Sector Is Enlarged By Hypoxia," International Journal of Radiation Oncology,Biology, Phyisics. 67(1):1-5 (2007).
Bristow et al., "Hypoxia and Metabolism. Hypoxia, DNA Repair and Genetic Instability," Nature Review Cancer. 8(3):180-182 (2008).
Brown et al., "The Hypoxic Cell: A Target for Selective Caner Therapy—Eighteenth Bruce F. Cain Memorial Award Lecture," Cancer Research. 59(23):5863-5870 (1999).
Chaplin et al., "Intermittent Blood Flow in a Murine Tumor: Radiobiological Effects," Cancer Research. 47(2):597-601 (1987).
Chi et al., "Gene Expression Programs in Response to Hypoxia: Cell Type Specifically and Prognostic Significance in Human Cancers," Plos Medicine. 3(3):47 (2006).
Clément et al., "Limits of CD133 as a Marker of Glioma Self Renewing Cells," International Journal of Cancer. 125(1):244-248 (2009).
Hall et al., Chapter 28. Radiobiology for the Radiobiologist. Charles W. Mitchell, 490-546 (2012).
Hall et al., Chapters 1-8. Radiobiology for the Radiobiologist. Charles W. Mitchell, 1-128 (2012).
Hall et al., Chapters 17-21. Radiobiology for the Radiobiologist. Charles W. Mitchell, 253-371 (2012).
Hall et al., Chapters 22-27 Radiobiology for the Radiobiologist. Charles W. Mitchell, 372-489 (2012).
Hall et al., Chapters 9-16. Radiobiology for the Radiobiologist. Charles W. Mitchell, 129-252 (2012).
Heldin et al., "High Interstitial Fluid Pressure—An Obstacle in Cancer Therapy," Nature Reviews Cancer. 4(10):806-813 (2004).
Intaglietta et al., "Dynamics of Microvascular Flow in Implanted Mouse Mammary Tumours," Bibliotheca Anatomica. 15(1):273-276 (1977).
International Preliminary Report on Patentability for International Application No. PCT/CA2018/051165, issued Mar. 24, 2020 (1 page).
International Search Report for International Application No. PCT/CA2018/051165, dated Dec. 6, 2018 (5 pages).
Jain, "Delivery of Molecular and Cellular Medicine to Solid Tumors," Microcirculation. 4:3-21 (1997).
Keith et al., "Hypoxia Inducible Factors, Stem Cells and Cancer," Cell. 129(3):465-472 (2007).
Lee et al., "New Developments in Radiation Therapy for Head and Neck Cancer: Intensity-Modulated Radiation Therapy and Hypoxia Targeting," Seminars in Oncology. 35(3):236-250 (2008).
Ma et al., "Celecoxib and Radioresistant Glioblastoma-Derived CD133+ Cells: Improvement in Radiotherapeutic Effects. Laboratory Investigation," Journal of Neurosurgery. 144(3):651-622 (2011).
McCall et al., "Copper-64-diacetyl-bis(N(4)-methylthiosemicarbazone) Pharmacokinetics in FaDu Xenograft Tumors and Correlation with Microscopic Markers of Hypoxia," International Journal of Radiation Oncology*Biology*Physics. 84(3): e393-e399 (2012).
Minchinton et al., "Drug Penetration in Solid Tumors," Nature Reviews Cancer. 6(8):583-592 (2006).
Nordsmark et al., "Pretreatment Oxygenation Predicts Radiation Response in Advanced Squamous Cell Carcinoma of the Head and Neck," Radiotherapy and oncology. 41(1):31-39 (1996).
Padera et al., "Pathology: Cancer Cells Compress Intratumour Vessels," Nature. 427(6976):695 (2004).
Seidel et al., "A Hypoxic Niche Regulates Glioblastoma Stem Cells Through Hypoxia Inducible Factor 2 Alpha," Brain. 133(4):983-995 (2010).
Stratton et al., "The Cancer Genome," Nature. 458:719-724 (2009).
Stypinski et al., "Clinical Pharmacokinetics of 123I-IAZA in Healthy Volunteers," Nuclear Medicine Commuincations. 20(6):559-567 (1999).
Written Opinion for International Application No. PCT/CA2018/051165, dated Dec. 6, 2018 (6 pages).
Office Action for Chinese Patent Application No. 201880074792, dated Feb. 8, 2023 (with English Translation, 17 pages).
Office Action for Canadian Patent Application No. 3,076,256, dated Oct. 15, 2024 (5 pages).
Office Action for Chinese Patent Application No. 201880074792, dated Oct. 24, 2023 (with English Translation) (11 pages).
Office Action for Chinese Patent Application No. 201880074792, dated Mar. 28, 2024 (with English Translation) (12 pages).
Office Action for Chinese Patent Application No. 201880074792.3, dated Oct. 12, 2024 (5 pages).
Notifications of Registration and Grant for Chinese Patent Application No. CN20188074792, dated Jan. 9, 2025 (with English Translation) (5 pages).

* cited by examiner

A B

MARKERS, CONJUGATES, COMPOSITIONS AND METHODS FOR HYPOXIA IMAGING, MAPPING, AND THERAPY

CROSS REFERENCE TO RELATED APPLICATION

This application claims priority to U.S. Patent Application 62/560,478, filed Sep. 19, 2017, the entire contents of which is hereby incorporated by reference.

FIELD

The present disclosure relates generally to markers, conjugates, compositions and methods for hypoxia imaging, mapping, and therapy.

BACKGROUND

Solid tumors frequently exhibit rapid growth and aberrant vasculature, leading to oxygen ($O_2$) depletion (hypoxia) and poor nutrient supply.[1-8] Hypoxia alters cellular metabolism, which can trigger transcriptional responses, induce genetic alterations[9-13] and activate the formation of transformed, self-renewing multipotent cancer stem cells (CSCs). Hypoxia promotes invasion, metastasis,[14,15] tumor progression and recurrence.[13,16-18] Hypoxic solid tumors are more resistant to radiotherapy and (due to impaired drug delivery)[6] to chemotherapy.[14,15,19-21] Tumor hypoxia thus poses a formidable challenge to therapeutic interventions and leads to poor local control and overall survival.[22, 23]

SUMMARY

In one aspect there is provided a compound of formula (I), or any prodrug, pharmaceutically acceptable salt, metabolite, polymorph, solvate, hydrate, stereoisomer, radioisotope or tautomer thereof (I)

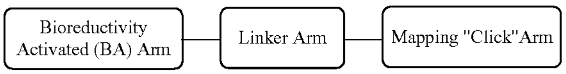

- wherein BA contains one or more of substituted or unsubstituted 2/4/5-substituted nitroimidazoles, or substituted benzotriazene-1,4-dioxides, or substituted 1,2,3/1,2,4-triazoles, or substituted 1,4-benzoquinones, or a combination of two homo-or hetero BA moieties,
- wherein BA may further be substituted with a macrocyclic ligand that can be linked to a reporting moiety—fluorescent biotinylating dye, or non-radioactive or radioactive halogen e.g. F, I etc., or a coordinating metal atom e.g. Ga-68, Tc-99m etc.,
- wherein linker arm contains $C_{1-22}$ alkane, alkene, alkyne, alicyclic or aromatic linkers with or without hetero atoms as in ethers, amine, esters, acid, amides, 5 and 6 membered sugar rings with the substitution as described above, both monosaccharides and disaccharides,
- wherein mapping click contains one of substituted or unsubstituted —$N_3$—, CN, SCN, substituted alkynes for click chemistry, which may further contain a reporting moiety,
- wherein clickable entities may also contain a macrocyclic ligand that can be unchelated or chelated with a metal-radioactive or non-radioactive-, or a radiohalogen for PET/SPECT, or a dye for fluorescent/optical reporting.

In one aspect, there is described a compound of formula (II), or any prodrug, pharmaceutically acceptable salt, metabolite, polymorph, solvate, hydrate, stereoisomer, radioisotope or tautomer thereof, (II)

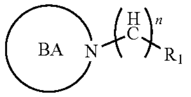

wherein

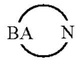

- is a bioreductively-activated moiety/nuclei, e.g., nitroimidazoles, benzotriazene-1,4-dioxides e.g., tirapazamine, and analogs thereof, substituted 1,2,4-traizoles, substituted tetrahydroisoquinolines, substituted benzoquinones e.g., AQ4N, and other examples of bioreductively activated nuclei
- wherein $R_1$ is unsubstituted, or substituted alicyclic, heterocyclic or open chain moiety with one or more —OH group, where one or more —OH group is substituted with alkyl, aralkyl ethers, esters, amines or thiols, remaining free —OH group is replaced by an —$N_3$/—CN—SCN/-alkyne/substituted alkyne/substituted alkane/alkene/alkyne/alkoxy/alkoxyalkyl/alkoxyalkenyl and alkoxyalkynyl chains,
- wherein —$N_3$/—CN—SCN/-alkyne/substituted alkyne groups may be conjugated with a reporting moiety, with a fluorescent dye or a radioactive halogen containing moiety,
- wherein n=($C_1$-$C_{22}$),
- wherein BA can be further substituted by a macrocyclic-substituted or unsubstituted ligands,
- wherein macrocyclic ligands may be substituted with a radiohalogen or coordinated with a metal ligand for reporting.

In one example, the sugar (all configurations) containing bioreductively activated molecules may further be substituted with an ether or ester moiety at 2'- and/or 3'-positions, and an azido/alkyne/halogen/pseudohalogen (F/I/OTosyl/ONosyl/OTriflyl/OMesyl) substituted at 2'- or 5' —OH of a sugar with or without a linker.

In one example, acyclic or cyclic substituents linked to the BA moieties are further substituted with $R_1$,

- wherein $R_1$=unsubstituted, or substituted alicyclic, heterocyclic or open chain moieties with one or more —OH groups, where one or more —OH group is substituted with alkyl, aralkyl ethers, esters, amines or thiols. Remaining free —OH group is replaced by an —$N_3$/—CN/—SCN/-alkyne/substituted alkyne/substituted alkane/alkene/alkyne/alkoxy/alkoxyalkyl/alkoxyalkenyl and alkoxyalkynyl chains.

In one example, the bioreductively-activated molecule includes nitroimidazole substituted, homo or hetero substituted acyclic or cyclic products e.g., azido-AZA (ACN), azido-MISO (AMI), azido containing quinolones, triazoles, tetrazoles, etc. and all related precursors; in benzotriazene-1,4-dioxide based molecules, the examples include tirapazamine (TPZ)-based acyclic or cyclic compounds, for example (C2/C4/C6 glucose-substituted-TPZ), and all related precursors to synthesize the corresponding halogenated (F,Cl,Br,I,At) derivatives.

In one example, said

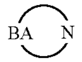

is

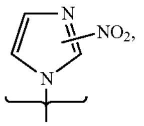

Azomycin Class

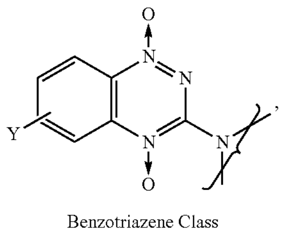

Benzotriazene Class

, or

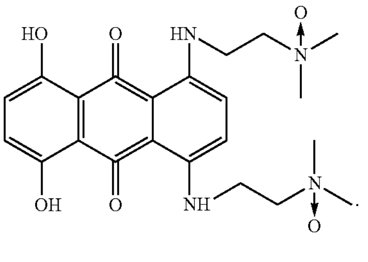

AQ4N Class

In one example, said benzotriazene class is

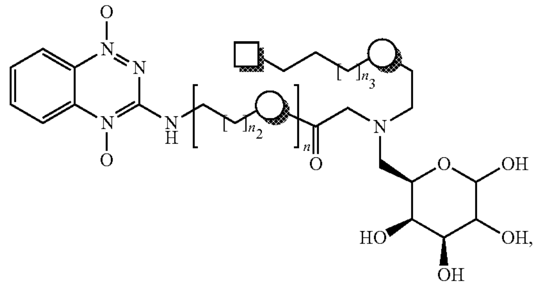

or

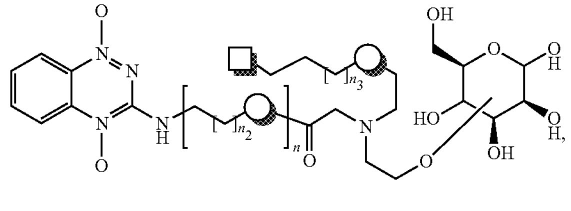

wherein $R_2$ is $N_3$, SCN, CN, Alkyne (substituted or unsubstituted), and alkenyl azide/CN/SCN, wherein $n_1$ is 1-22, wherein $n_2$ is 1-22, wherein $n_3$ is 1-22.

In one aspect there is described a compound of formula (III), or any prodrug, pharmaceutically acceptable salt, metabolite, polymorph, solvate, hydrate, stereoisomer, radioisotope or tautomer thereof,

Y-L-BA (III)

wherein BA is a bioreductively-activated moiety/nuclei, e.g., nitroimidazoles, benzotriazene-1,4-dioxides e.g., tirpazamine, and analogs thereof, substituted 1,2,4-triazoles, substituted tetrahydroisoquinolines, substituted benzoquinones e.g. AQ4N that are substituted with $R_1$, or any other bioreductively activated moiety wherein $R_1$ is C1-α/β-substituted arabinofuranoses/pentoses/hexoses (e.g., glucose, disaccharide etc.) where other —OH groups except one in the sugar ring are either unsubstituted, or substituted with alkyl, aralkyl ethers, esters, amines or thiols, remaining free —OH group is replaced by an azide or an alkyne—substituted or unsubstituted, wherein $R_1$ is $R_2$-substituted alkane/alkene/alkyne/alkoxy/alkoxyalkyl/alkoxyalkenyl and alkoxyalkynyl chains ($C_1$-$C_{22}$), $R_2$ is azide, alkyne, or biotinylated alkyne, wherein Y is a ligand (e.g., a tetradentate ligand as in DOTA or NOTA) containing an azide or alkyne substituted linked, with or without a linker "L", the bioreductive drugs BA; a ligand may be coordinated to a metal prior to coupling with BA or afterwards, wherein L is a linker cyclic or acyclic with up to $C_{22}$ chains.

In one aspect there is described a radiolabeled compound of the disclosure, wherein said radiolabelling method is a manual method or an automated method.

In one aspect there is described a pharmaceutical comprising a compound of the disclosure, or a radiolabeled compound thereof, and one or more inert carriers and/or diluents.

In one aspect there is described a use of a compound of the disclosure, a radiolabeled compound thereof, or a pharmaceutical composition thereof, as a diagnostic agent in a subject.

In one aspect there is described a compound of the disclosure, a radiolabeled compound thereof, or a pharmaceutical composition thereof, as a therapeutic agent in a subject.

In one aspect there is described a compound of the disclosure, a radiolabeled compound thereof, or a pharmaceutical composition thereof, as a diagnostic and therapeutic agent in a subject.

In one aspect there is described a compound of the disclosure, a radiolabeled compound thereof, or a pharmaceutical composition thereof, as an imaging agent in a subject.

In one aspect there is described a compound of the disclosure, a radiolabeled compound thereof, or a pharmaceutical composition thereof, as a radiosensitization agent in a subject.

In one aspect there is described a compound of the disclosure, a radiolabeled compound thereof, or a pharmaceutical composition thereof, as a chemosensitization agent in a subject.

In one aspect there is described a compound of the disclosure, a radiolabeled compound thereof, or a pharmaceutical composition thereof in molecular radiotherapy (MRT), also known as systemic radioisotope therapy (SRT) and endoradiotherapy (ERT), chemosensitization therapy, radiosensitization therapy, auger therapy, or hypoxia imaging.

In one example, wherein (a) said imaging is fluorescence, optical, MRI, radioactive PET and SPECT, PET imaging for example using F-18, 1-124, Ga-68, SPECT using e.g., I-131 and I-123, optical imaging using fluorescent dyes; therapeutic uses include chemotherapy (e.g., I-127, F-19, and other non-radioactive compounds); Auger Therapy (I-125), photodynamic therapy (PDT), radiosensitization, and Molecular Radiotherapy [MRT; I-131, Lu-177, Re-186 but not limited to these isotopes]) (b) theranostic uses (PET and SPECT imaging, MRI, fluorescence, optical, PDT, radiosensitization, MRT).

In one example, wherein said subject is a human or any living model

In one aspect there is described a method of detecting hypoxia in cells, comprising: applying to a subject a compound of the disclosure, or a pharmaceutical composition thereof; and b) detecting the presence of retained radioactive element in hypoxic cells of the subject.

BRIEF DESCRIPTION OF THE FIGURES

Embodiments of the present disclosure will now be described, by way of example only, with reference to the attached Figures.

DETAILED DESCRIPTION

Figure 1:
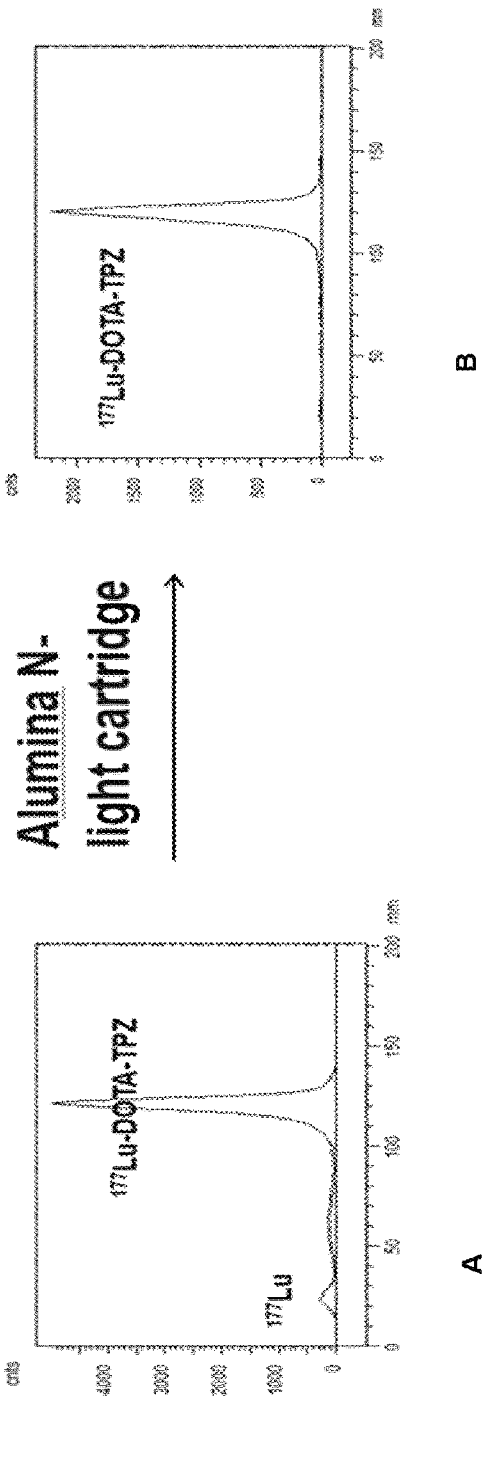
FIG. 1 depicts the chromatograms of pre-(Panel A) and post-solid phase (Panel B) extraction (SPE) of radioactive $^{177}$Lu-labelled DOTA-TPZ as an example to use SPE method for purifying radioactive compounds of Class IV.

Unless defined otherwise, all technical and scientific terms used herein have the same meaning as commonly understood by one of ordinary skill in the art to which this disclosure belongs.

As used herein, the term "hydrocarbon," used alone or in combination, refers to a linear, branched or cyclic organic moiety comprising carbon and hydrogen, for example, alkyl, alkene, alkyne, and aryl, which may each be optionally substituted. In some examples, a hydrocarbon may, for example, comprise about 1 to about 60 carbons, about 1 to about 40 carbons, about 1 about 30 carbons, about 1 about 20 carbons, about 1 to about 10 carbons, about 1 to about 9 carbons, about 1 to about 8 carbons, about 1 to about 6 carbons, about 1 to about 4 carbons, or about 1 to about 3 carbons. In some embodiments, hydrocarbon comprises 10 carbons, 9 carbons, 8 carbons, 7 carbons, 6 carbons, 5 carbons, 4 carbons, 3 carbons, 2 carbons, or 1 carbon.

As used herein, the term "alkyl" refers to straight or branched hydrocarbon. An alkyl may be linear, branched, cyclic, or a combination thereof, and may contain, for example, from one to sixty carbon atoms. Examples of alkyl groups include but are not limited to ethyl, ethyl, propyl, isopropyl, cyclopropyl, butyl isomers (e.g. n-butyl, iso-butyl, tert-butyl, etc.) cyclobutyl isomers (e.g. cyclobutyl, methylcyclopropyl, etc.), pentyl isomers, cyclopentane isomers, hexyl isomers, cyclohexane isomers, and the like.

As used herein, the term "linear alkyl" refers to a chain of carbon and hydrogen atoms (e.g., ethane, propane, butane, pentane, hexane, etc.). A linear alkyl group may be referred to by the designation $—(CH_2)_qCH_3$, where q is, for example, 0-59. The designation "$C_{1-12}$ alkyl" or a similar designation, refers to alkyl having from 1 to 12 carbon atoms such as methyl, ethyl, propyl isomers (e.g. n-propyl, isopropyl, etc.), butyl isomers, cyclobutyl isomers (e.g. cyclobutyl, methylcyclopropyl, etc.), pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc. Similar designations refer to alkyl with a number of carbon atoms in a different range.

As used herein, the term "branched alkyl" refers to a chain of carbon and hydrogen atoms, without double or triple bonds that contains a fork, branch, and/or split in the chain. "Branching" refers to the divergence of a carbon chain, whereas "substitution" refers to the presence of non-carbon/non-hydrogen atoms in a moiety.

As used herein, the term "cycloalkyl" refers to a completely saturated mono- or multi-cyclic hydrocarbon ring system. When composed of two or more rings, the rings may be joined together in a fused, bridged or spiro-connected fashion. A cycloalkyl group may be unsubstituted, substituted, branched, and/or unbranched. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. Unless specified otherwise (e.g., substituted cycloalkyl group, heterocyclyl, cycloalkoxy group, halocycloalkyl, cycloalkylamine, thiocycloalkyl, etc.), an alkyl group contains carbon and hydrogen atoms only.

As used herein, the term "heteroalkyl" refers to an alkyl group, wherein one or more carbon atoms are independently replaced by one or more heteroatoms (e.g., oxygen, sulfur, nitrogen, phosphorus, silicon, or combinations thereof). The alkyl group containing the non-carbon substitution(s) may be a linear alkyl, branched alkyl, cycloalkyl (e.g., cycloheteroalkyl), or combinations thereof. Non-carbons may be at terminal locations (e.g., 2-hexanol) or integral to an alkyl group (e.g., diethyl ether).

The term "alkoxy", used alone or in combination, means the group —O— alkyl.

The term "alkenyl", used alone or in combination, means a straight or branched chain hydrocarbon having at least 2 carbon atoms, which contains at least one carbon-carbon double bond.

The term "haloalkyl" refers to an alkyl in which one or more hydrogen has been replaced with same or different halogen.

The term "alkynyl", used alone or in combination, means a straight or branched chain hydrocarbon having at least 2 carbon atoms, which contains at least one carbon-carbon triple bond.

The term "alkoxyalkyl" means a moiety of the formula -R'-R", where R' is alkylene and R" is alkoxy.

The term "aryl", used alone or in combination, means an aromatic carbocyclic moiety of up to 60 carbon atoms, which may be a single ring (monocyclic) or multiple rings fused together (e.g., bicyclic or tricyclic fused ring systems).

The term "alkylene" refers to divalent aliphatic hydrocarbyl groups preferably having from 1 to 6 and more preferably 1 to 3 carbon atoms that are either straight-chained or branched.

The terms "amine" or "amino" as used herein are represented by a formula NA1A2A3, where A1, A2, and A3 can be, independently, hydrogen or optionally substituted alkyl, cycloalkyl, alkenyl, cycloalkenyl, alkynyl, cycloalkynyl, aryl, or heteroaryl group as described herein. In specific embodiments amine refers to any of $NH_2$, NH(alkyl), NH(aryl), $N(alkyl)_2$, N(alkyl)(aryl), and $N(aryl)_2$.

As used herein, the term "substituted" means that the referenced group (e.g., alkyl, aryl, etc.) comprises a substituent group. The term "optionally substituted", as used herein, means that the referenced group (e.g., alkyl, cycloalkyl, etc.) may or may not be substituted with one or more additional group(s).

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $Rx \cdot H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot_{0.5} H_2O$)), and polyhydrates (x is a number greater than 1, e.g., dihydrates ($R \cdot_2 H_2O$) and hexahydrates ($R \cdot 6\ H_2O$)).

The term "tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds described herein, which have cleavable groups and become by solvolysis or under physiological conditions the compounds described herein, which are pharmaceutically active in vivo.

As used herein, "derivative" refers to any compound having the same or a similar core structure to the compound but having at least one structural difference, including substituting, deleting, and/or adding one or more atoms or functional groups.

The term "derivative" does not mean that the derivative is synthesized from the parent compound either as a starting material or intermediate, although this may be the case.

The term "metabolite" includes any compound into which a compound as described here can be converted in vivo once administered to the subject.

The term "subject", may refer to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

The terms "administer," "administering," or "administration" refers to implanting, absorbing, ingesting, injecting, inhaling, or otherwise introducing an inventive compound, or a pharmaceutical composition thereof, in or on a subject.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein, such as a fungal or protozoan infection. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

A "therapeutically effective amount" of a compound or composition described herein is an amount sufficient to provide a therapeutic benefit in the treatment of a condition or to delay or minimize one or more symptoms associated with the condition. A therapeutically effective amount of a compound or composition means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound or composition described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "pharmaceutical composition" refers to the combination of an active agent with a carrier, inert or active, making the composition suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

The term "sample" or "biological sample" refers to any sample including tissue samples (such as tissue sections and needle biopsies of a tissue); cell samples (e.g., cytological smears or samples of cells obtained by microdissection); samples of whole organisms; or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

The term "radiosensitizer", as used herein, refers to a compound or composition, which when administered to a subject in therapeutically effective amounts, to increase the sensitivity of the cells to ionizing radiation and/or to promote the treatment of diseases which are treatable with ionizing radiation.

In some examples, non-limiting examples of radiation therapy include external beam radiation therapy (EBRT or XRT), tele therapy, brachytherapy, sealed source radiation therapy, systemic radioisotope therapy (RIT; also called SRT), unsealed source radiation therapy, intraoperative radiation therapy (IORT), targeted intraoperative radiation therapy (TARGIT), intensity-modulated radiation therapy (IMRT), volumetric modulated arc therapy (VMAT), particle therapy, and auger therapy.

The term “chemosensitizer”, as used herein, refers to a compound of composition, which when administered to a subject in therapeutically effective amounts, to increase the sensitivity of cells to chemotherapy and/or promote the treatment of diseases which are treatable with chemo therapeutics.

The term “fluorescent dye” as used herein refers to moieties that absorb light energy at a defined excitation wavelength and emit light energy at a different wavelength.

In one example, the term “radiochemical” as used herein refers to an organic, inorganic or organometallic compound comprising a covalently-attached radioactive isotope, inorganic radioactive ionic solution, or radioactive gas, particularly including radioactive molecular imaging probes intended for administration to a patient (e.g., by inhalation, ingestion or intravenous injection) for tissue imaging purposes, which are also referred to in the art as radiopharmaceuticals, radiotracers or radioligands.

The term “radioactive isotope” or “radioactive element” refers to isotopes exhibiting radioactive decay (i.e., emitting positrons) and radiolabeling agents comprising a radioactive isotope.

Isotopes or elements are also referred to in the art as radioisotopes or radionuclides.

Radioactive isotopes are named herein using various commonly used combinations of the name or symbol of the element and its mass number (e.g., $^{18}F$, F-18, or fluorine-18). Non-limiting examples of radioactive isotopes include 1-124, F-18 fluoride, C-11, N-13, and O-15, I-123, I-124, I-127, I-131, Br-76, Cu-64, Tc-99m, Y-90, Ga-67, Cr-51, Ir-192, Mo-99, Sm-153 and Tl-201. Other examples of radioactive isotopes include: As-72, As-74, Br-75, Co-55, Cu-61, Cu-67, Ga-68, Ge-68, I-125, I-131, In-111, Mn-52, Pb-203 and Ru-97.

As used herein, the term “theranostic” refers to a combination of a specific therapy and diagnostic.

As used herein in connection with a measured quantity, the term “about” refers to the normal variation in that measured quantity that would be expected by the skilled artisan making the measurement and exercising a level of care commensurate with the objective of the measurement and the precision of the measuring equipment used. Unless otherwise indicated, “about” refers to a variation of +/−10% of the value provided.

Generally, described herein is the development of innovative bioreductively-activated products as shown in Scheme (1)

(I)

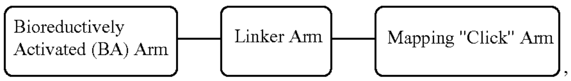

, their synthesis processes, compositions and their applications in therapy and diagnostic (theranostic) imaging and mapping of cellular/tissue hypoxia in tumors (oncological diseases) and in other pathophysiological diseases demonstrating hypoxia, for example in diabetes, stroke, myocardial infarction, concussion and inflammatory disorders.

In some examples, molecules developed herein are Tirapazamine (TPZ)-based and azomycin nucleoside-based azides and acetylenic derivatives and their macrocyclic analogs with or without coordination with metal chelates. These molecules when “clicked” with a “Reporting” entity facilitate cellular and molecular mapping of molecular and cellular hypoxia in cancerous tumor regions. The molecules also reveal the extent of hypoxia, identification of the protein(s) that are expressed in hypoxic conditions and get conjugated with the bioreductive drugs, and the extent of accrual of bioreductive drugs within diseased cells before and after therapy, and the identification of the molecular binding proteins that are expressed in hypoxic conditions.

In one case, these compounds (Scheme 2), when reduced in hypoxic cells, bind by click chemistry to biotin alkynes in situ that can be conveniently imaged by non-invasive fluorescent, or optical, imaging. Click reagents include biotin alkyne, biotin azides, streptavidin, any appropriately derivatized fluorescent or optical “reporter”, radioactive, magnetic resonance sensitive, or any other reportable probe chemical or a coordinating metal. Irreversible covalent binding of our molecules selectively to cytoplasmic macromolecules, nuclear, nucleolar, and mitochondrial contents in a hypoxic cell demonstrates a highly innovative and commercially viable technique to map and image hypoxia within the cell, nuclei, nucleoli in vitro, and also in vivo in preclinical and possibly medical imaging, when click chemistry is performed. The technique is fast, simple and does not involve any secondary antibody as in case of Pimonidazole-based immunohistochemical (IHC) staining.

In another case, these compounds can be labelled with a radioactive or non-radioactive metal, transition or non-transition, by a chemical reaction, which can be detected in vivo by a medical imaging technique, for example, magnetic resonance imaging (MRI) by coordinating these molecules with Gadolinium, positron emission tomography (PET) imaging using Gallium-68 and single photon emission computed tomography (SPECT) imaging e.g., using Technitium-99m. Being bioreductively-activated, the molecules also bestow hypoxia-selective chemotherapeutic properties, photodynamic therapy (PDT) when attached to an element or compound that is activated by a light source, ultrasound activation therapy, for example activation by acoustic sources, radiotherapy, and also radiosensitization therapy in conjunction with conventional radiotherapy. Thus, the invention proposed here offers a ‘single molecule’ approach to an effective multimodal non-invasive theranosis of hypoxic tumors. The molecules are also useful in imaging several other diseases that demonstrate physiological hypoxia, including diabetes, inflammatory arthritis, anaerobic bacterial infections, stroke, brain trauma and transplant rejection, and potential therapy.

The general structure of the compounds described in Scheme 2 include a bioreductively-activated (BA) moiety-derived acyclic molecules, e.g., 2/4/5-nitroimidazoles (as in F-MISO), or substituted with cyclic moieties, or sugar substituted moieties (both pentoses as in FAZA [substituted or unsubstituted] and IAZA [substituted or unsubstituted], and hexoses, disaccharides and trisaccharides in all configurations; for example, as in glucoses, galactoses, fructoses, other substituted moieties). Examples of other BA arms claimed under the invention include substituted or unsubstituted benzo-1,2,4-triazene-1,4-dioxides (e.g., substituted tirapazamines); substituted benzoquinones e.g., as in AQ4N, substituted triazoles as in HX4, their precursors, and their derivatives.

Scheme 2.
General formula 1 of the compounds and the substituents described under Claim 1

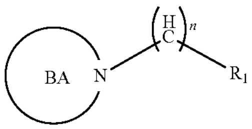

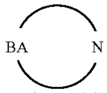

1. = ALL bioreductively-activated moities/nuclei e.g., nitroimidazoles, benzotriazene-1,4-dioxides e.g., tirapazamine, and its all analogs, substitutted 1,2,4-triazoles, substituted tetrahydroisoquinolines, substituted benzoquinones e.g., AQ4N
2. $R_1$ = unsubstituted, or substituted alicyclic, heterocyclic or open chain moities with one or more -OH groups, where one or more -OH group is substituted with alkyl, aralkyl ethers, esters, amines or thiols. Remaining free -OH group is replaced by an -$N_3$/-CN/-SCN/-alkyne/substituted alkyne/substituted alkane/alkene/alkyne/alkoyl/alkoxyalkyl/alkoxyalkenyl and alkoxyalkynyl chains
3. $N_3$/-CN/-SCN/-alkyne/substituted alkyne groups can be conjugated to a "reporting moiety" with a fluorescent dye, or a radioactive halogen containing moiety
3. n = ($C_1$—$C_6$);
4. BA can be further substituted by a macrocyclic-substituted or unsubstituted ligands;
5. Macrocyclic ligands may be substituted with a radiohalogen, or coordinated with a metal ligand for "reporting"

Sugar (all configurations) containing bioreductively activated molecules described above may further be substituted with an ether or ester moiety at 2' and/or 3' positions, and an azido/alkyne/halogen/pseudohalogen (F/I/OTosyl/ONosyl/OTriflyl/OMesyl) substituted at 2'- or 5'-OH of a sugar with or without a linker (Scheme 2);

Acyclic or cyclic substituents linked to the BA moieties are further substituted with R1, where R1=unsubstituted, or substituted alicyclic, heterocyclic or open chain moieties with one or more —OH groups, where one or more —OH group is substituted with alkyl, aralkyl ethers, esters, amines or thiols. Remaining free —OH group is replaced by an —$N_3$/—CN/—SCN/-alkyne/substituted alkyne/substituted alkane/alkene/alkyne/alkoxy/alkoxyalkyl/alkoxyalkenyl and alkoxyalkynyl chains.

Examples of bioreductively activated molecules include nitroimidazole substituted, homo or hetero substituted acyclic or cyclic products e.g., azido-AZA (ACN), azido-MISO (AMI), azido containing quinolones, triazoles, tetrazoles, etc. and all related precursors; in benzotriazene-1,4-dioxide based molecules, the examples include tirapazamine (TPZ)-based acyclic or cyclic compounds, for example (C2/C4/C6 gluc substituted-TPZ), and ALL related precursors to synthesize the corresponding halogenated (F,Cl,Br,I,At) derivatives. Claims on bioreductively activated molecules is however not limited to these classes.

Non-limiting examples the classes of bioreductively activated cores are described in Scheme 3.

Scheme 3.
Where, $R_2$ = $N_3$, SCN, CN, Alkyne (substituted or unsubstituted), an alkenyl azide/CN/SCN; $n_1$, $n_2$ or $n_3$ = 1-22

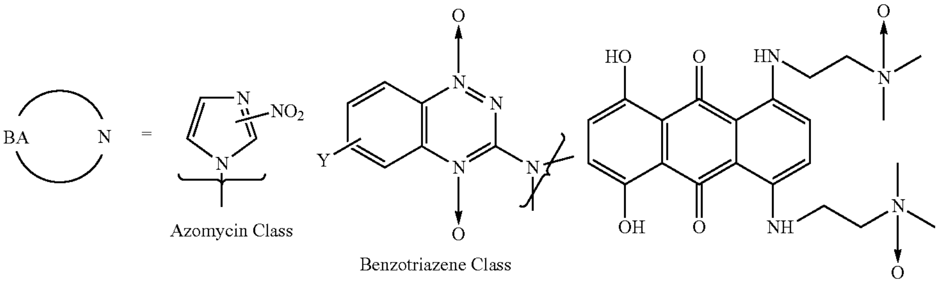

Azomycin Class

Benzotriazene Class

AQ4N Class

For example, in case of Benzotriazene class, General Formula 1 is further elaborated as below.

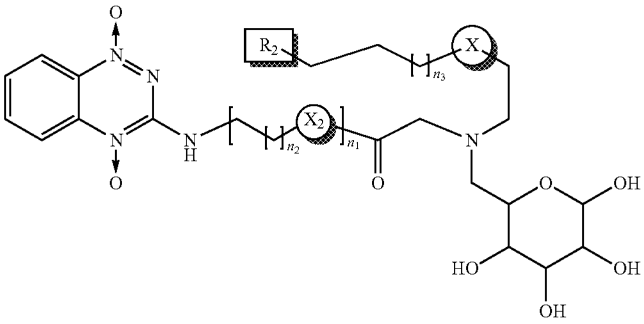

and

-continued

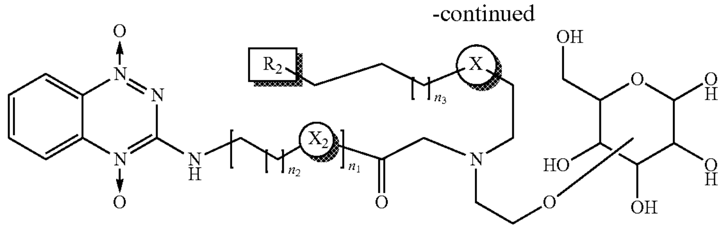

Embodiments from the classes of the BA drugs synthesized covered by the general formula 1 (Scheme 3) are provided below.

Class 1: Azido or Alkyne Substituted α/β-AZAs

Example of the compound synthesized under this class include 5'-azido-arabinofuranosyl-2-nitroimidazole (ACN, Compound 1) and its 2'3'-di-O-pivaloyl analog (Compound 2)

Scheme 4.
Schema for synthesizing ACN (1) and its dipivaloyl analog as the representatives of this class

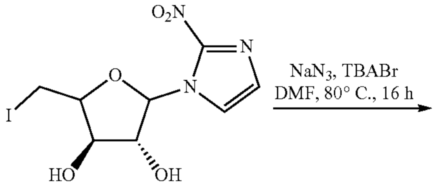

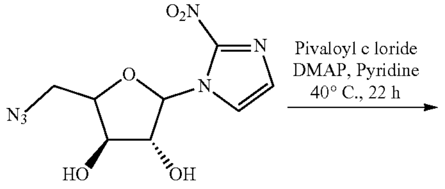

I

Chemical Formula: $C_9H_1N_6O_5$
Exact Mass: 270.07
Molecular Weight: 270.21

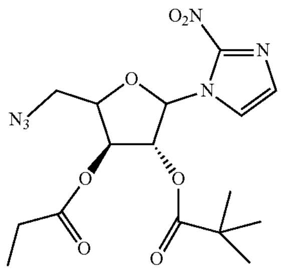

2

Chemical Formula: $C_8H_{20}N_6O_7$
Exact Mass: 408.19
Molecular Weight: 438.44

Synthesis of 1-α-D- (5'-azidoarabinofuranosyl-2-nitroimidazole) (ACN)

ACN was synthesized by two methods.

In one method (shown in Scheme 4), Sodium azide ($NaN_3$, 0.91 g, 10 Eq, 14.0 mmol), and tetra-n-butylammonium bromide (TBAB, 0.27g, 0.6 Eq, 0.8 mmol) were added to the solution of IAZA in DMF and stirred at 75 □C for 15 hr. Progress of the reaction was monitored by TLC. Water was added to the reaction mixture and crude product was extracted with ethyl acetate (3×20 mL). All the collected organic layers were dried over $Na_2SO_4$ and evaporated to dryness under reduced pressure. The obtained crude product was purified by silica-gel column chromatography using dichloromethane and methanol in 8:2 ratio as an eluent, which afforded pale yellow colored product (70%).

Alternatively, AZA-tosylate (0.028 g, 0.07 mmol, 1 eq) and sodium azide (0.0455 g, 0.70 mmol) were dissolved in DMSO (5 mL) and heated to 50° C. overnight (16 h). After cooling the reaction mixture to 22-25° C., water (10 mL) was added to quench the reaction and the product was extracted in ethyl acetate (3×10 mL). The combined organic extracts were dried over anhydrous sodium sulfate, filtered and evaporated to afford 13 mg (0.048 mmol, 69% yield) of ACN. $^1H$ NMR (498 MHz, $CD_3OD$) δ7.66 (dd, J=1.3, 0.5 Hz, 1H, imidazole H-5), 7.13 (d, J=1.3 Hz, 1H, imidazole H-4), 6.46 (d, J=1.4 Hz, 1H, H-1'), 4.60-4.51 (m, 1H, H-2'), 4.29 (dd, J=2.0, 1.5 Hz, 1H, H-3'), 4.07 (t, J=2.3 Hz, 1H, H-4'), 3.64 (dd, J=12.9 Hz, 7.4 Hz, 1H, H-5'), 3.48 (dd, J=12.9, 7.4 Hz, 1H, H-5'), ppm; $^{13}C$ NMR (101 MHz, $CD_3OD$) δ 144.00 (imidazole C-2), 127.98 (nitroimidazole C-4), 125.04 (nitroimidazole C-5), 96.76 (C-1'), 89.69 (C-2'), 83.50 (C-3'), 78.33 (C-4'), 53.57 (C-5') ppm; HR-MS (ESI): m/z: 293.0599 [M+Na]+.

Class II: Azido or Alkyne Substituted Benzo-1,2,4-Triazene-1,4-Dioxides

Subclass II.1

Examples of the compounds synthesized under this class include 3-(2-(2-azidoethoxy)ethyl)amino-1,2,4-benzotriazine 1,4-dioxide (AEEA-TPZ; 3, where Nu=$-N_3$) and the related derivatives, where X=—CN, SCN, alkyne—substituted or unsubstituted, but not limited to these moieties (Scheme 1). Characterization data for compound 3 are provided below.

Scheme 5. Schema to synthesize Compound 3

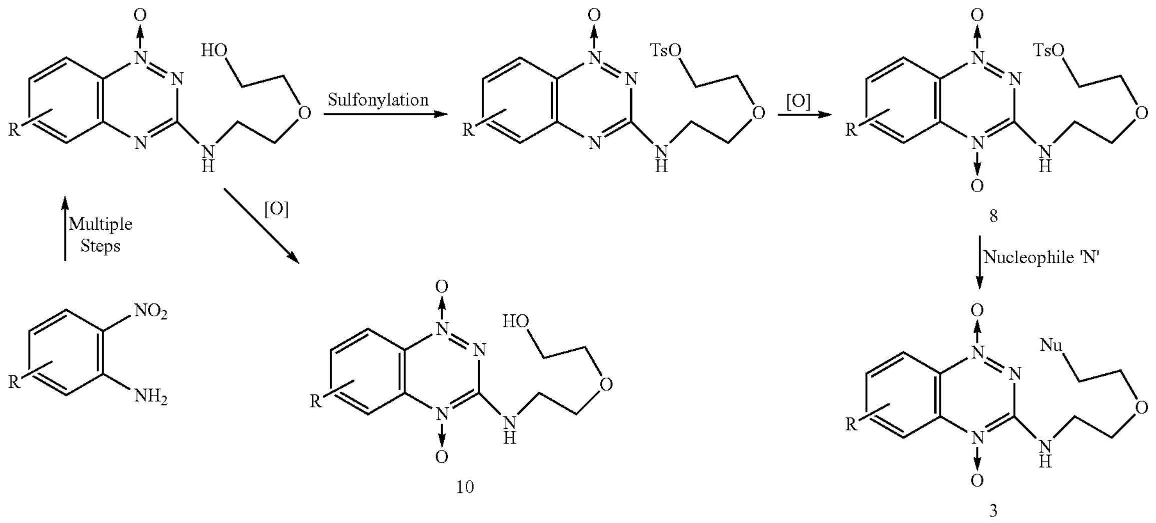

Where R—H, a substituted or unsubstituted aklyl/aralkyl/alicyclic, hetrocyclic, ethers, esters, azide, amines, amides, thioethers, sulfonyl esters, halogens; R-substituted pentoses, hexoses, monosachharides, disaccharides, but not limited to the described substitutents;
Nu—R, an alkyne, fluorscent biotinaylated aklyne, azide, or any nucleophile

Synthesis of 3-(2-(2-Azidoethoxy)ethyl)amino-1,2,4-benzotriazine 1,4-dioxide (ATZ; 3)

A solution of 8 (100 mg, 0.24 mmol) and $NaN_3$ (46.4 mg, 0.71 mmol) in DMF (2 mL) was heated at 100° C. for 1 h. The solution was quenched with cold $H_2O$ (20 mL) and extracted in $CH_2Cl_2$ (2×20 mL). The organic layer was concentrated under reduced pressure and the crude residue was purified with chromatography (10:1 EtOAc-$CH_3OH$, v/v) yielding ATZ, 3 (59.6 mg, 86%) as a red solid; $^1H$ NMR (400 MHz, $CDCl_3$, δH) 8.33-8.22 (m, 2H, Ar), 7.84 (ddd, J=8.6, 7.0, 1.3 Hz, 1H, Ar), 7.48 (ddd, J=8.7, 7.0, 1.2 Hz, 1H, Ar), 3.81 (q, J=5.3 Hz, 2H, CH2), 3.73 (t, J=4.8 Hz, 2H, CH2), 3.70-3.64 (m, 2H, CH2), 3.40-3.33 (m, 2H, CH2); $^{13}C$ NMR (101 MHz, $CDCl_3$, δC) 149.77, 138.29, 135.74, 130.52, 127.27, 121.59, 117.42, 70.09, 69.24, 50.60, 41.21.

SUBCLASS II.2. Examples of the compounds synthesized under this subclass include various sugars conjugated at C6 position to 1,2,4-benzotriazine 1,4-dioxide (or other bioreductive moities as described in Scheme 3) via a linker that is substituted to a 'mapping' or 'therapy' arm (G6-A-TPZ; Scheme 6 Schema, where Nu=—$N_3$), and the related derivatives, where X=—CN, —SCN, alkyne—substituted or unsubstituted, but not limited to these moities (Scheme 3). Characterization data for compound 17 (G6-A-TPZ) are provided below.

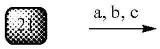

-continued

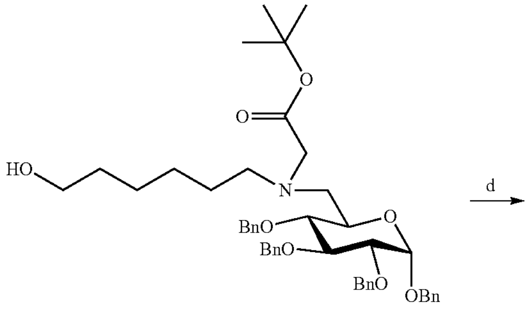

35

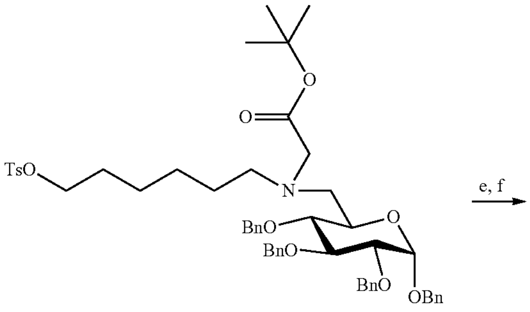

36

-continued

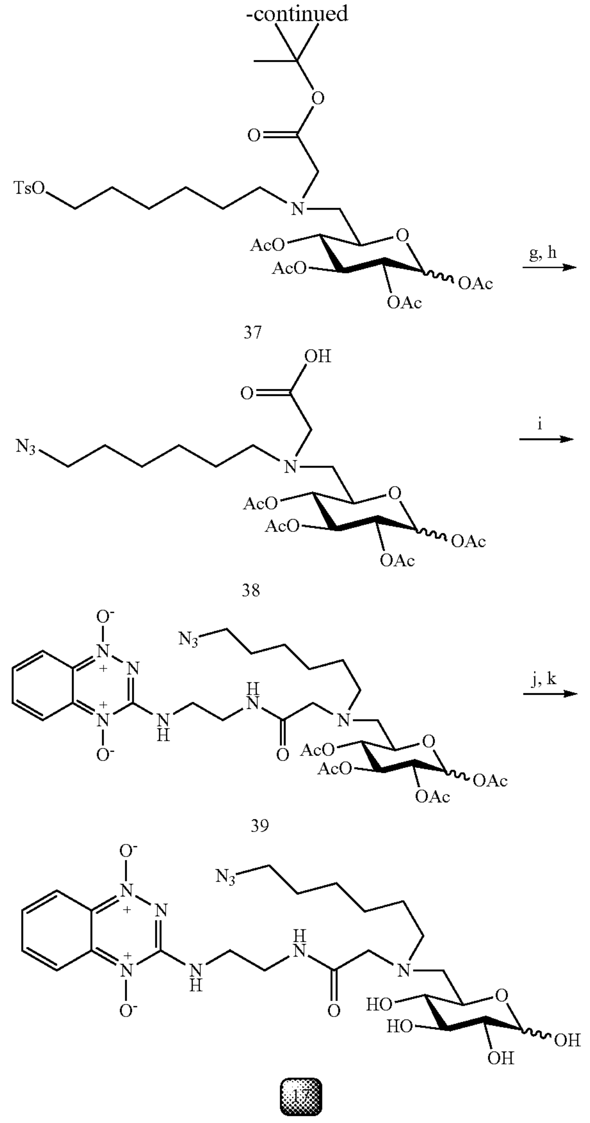

37

38

39

17

Reagents and conditions: (a) $(TfO)_2O$, DIEA, DCM, −40° C., 30 min, (b) 22, 5 h; $H_2O$, 82% over two steps; (c) $BrCH_2COOtertBu$, DIEA, DCM, overnight, 67%; (d) TsCl, DCM, DMAP, $Et_3N$, 1 h, 83%; (e) Pd/C, $H_2$, DCM/MeOH, overnight; (f) $Ac_2O$, pyridine, 2 h, 87% over two steps; (g) $NaN_3$ DMF, 80° C., 1 h; (h) TFA-DCM (1:1), 2 h, 79% over two steps; (i) 23, EDC, HOBt, DCM, DIEA, 4 h, 84%; (j) $CH_3ONa$, DCM/MeOH, 30 min; (k) Acidic resin work-up, 71% over two steps.
Scheme 6. Schema to synthesize Compound 17 as a representative of the sub-class II.2.

Synthesis of Compound 17

Compound 17: Multistep synthesis was performed using the synthesis reagents and conditions to obtain compound 17 in 71% yield. HRMS (ESI) for $(M+Na)^+$ $C_{23}H_{35}N_9NaO_8$: Calcd. 588.2501. Found: 588.2495. HRMS (ESI) Calcd. for $(M+H)^+$ $C_{23}H_{36}N_9O_8$: 566.2681. Found: 566.2673.

Subclass II.3

Examples of the compounds synthesized under this subclass include various sugars conjugated at C2 position to 1,2,4-benzotriazine 1,4-dioxide (or other bioreductive moieties as described in FIG. 3) via a linker that is substituted to a 'mapping' or 'therapy' arm (G2-A-TPZ; Scheme. 7 Schema), and the related derivatives, where X=—CN, —SCN, alkyne—substituted or unsubstituted, but not limited to these moities (Scheme. 3). Characterization data for compound 19 (G2-A-TPZ) are provided below.

Scheme 7. Schema to synthesize Compound 19 (G2-A-TPZ) as a representative of the sub-class II.3.

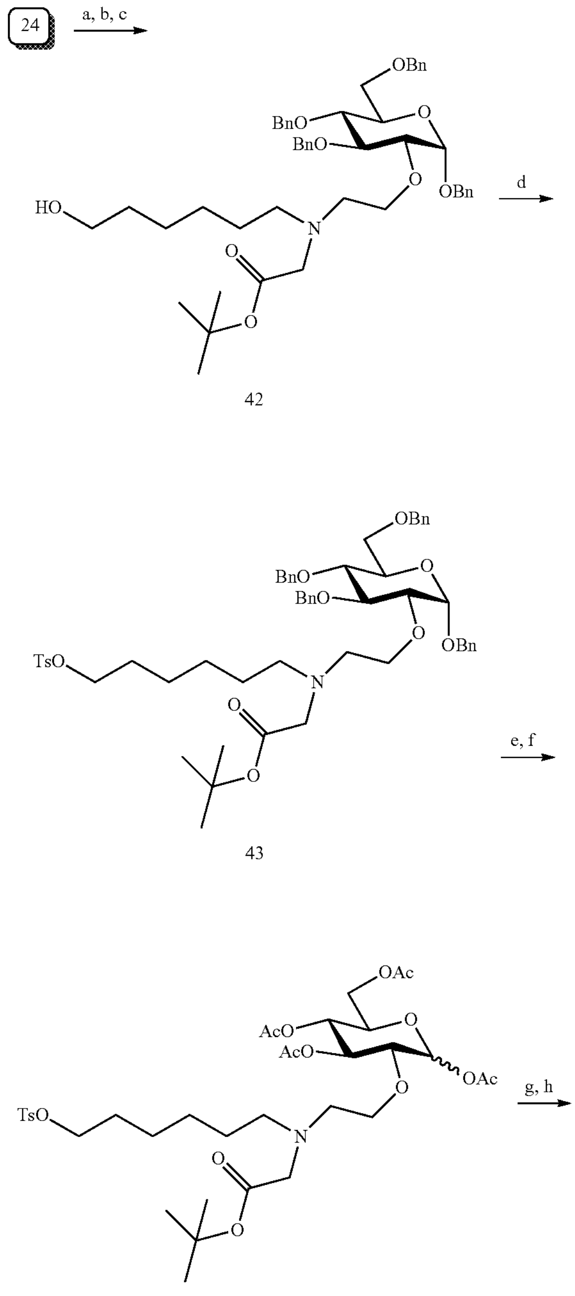

42

43

44

-continued

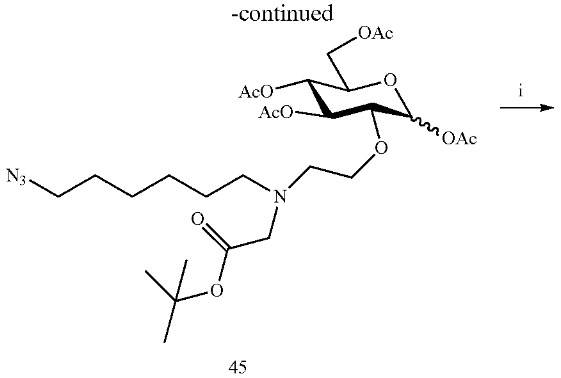

45

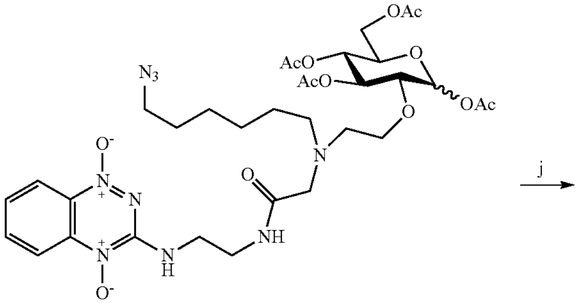

46

-continued

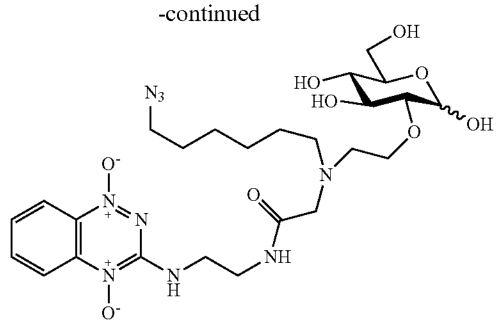

19

Reagents and conditions: (a) $Tf_2O$, DIEA, DCM, -40° C., 30 min; (b) 22, 5 h; $H_2O$, 82%; (c) $BrCH_2COOtertBu$, DIEA, DCM, overnight, 67%; (d) TsCl, DCM, DMAP, TEA, 1 h, 74%; (e) Pd/C, $H_2$, DCM/MeOH, overnight; (f) $Ac_2O$, pyridine, 2 h, 73% over two steps; (g) $NaN_3$ DMF, 60° C., 1 h; (h) TFA—DCM (1:1), 2 h, 85% over two steps; (i) 23, EDC•HCl, HOBt, DCM, DIEA, 4 h, 64%; (j) $CH_3ONa$, DCM/MeOH, 30 min, 68%.

Compound 19: Multistep synthesis was performed using the synthesis reagents and conditions described for FIG. 7 to obtain this compound in 68% yield. HRMS (ESI) Calcd. for $(M+Na)^+$ $C_{25}H_{39}N_9NaO_9$: 632.2763. Found: 632.2757. HRMS (ESI) Calcd. for $(M+H)^+$ $C_{25}H_{40}N_9O_9$: 610.2944. Found: 610.2936.

In one example, a general Formula for the (Radio)pharmaceuticals synthesized under this class is provided below.

| | |
|---|---|
| Y-L-BA | 1. BA = All bioreductively-activated moities/nuclei e.g., nitroimidazoles, benzotriazene-1,4-dioxides e.g., tiraparamine, and its all analogs, substituted 1.2.4-triazoles, substituted tetrahydroisoquinolines. substituted benzoquinones e.g., AQ4N that are substitutted with $R_1$<br>2. $R_1$ = C7-α/β substituted arabinofuranoses/pentoses/hexoses (e.g., glucose, disaccharide etc., ) where other —OH groups except one in the sugar ring are either unsubstituted. or substituted with alkyl, aralkyl ethers. esters, amines or thiols, Remaining free —OH group is replaced by an azide or an alkyne-substituted or unsubstituted.<br>3. $R_1$ = $R_2$-substituted alkane/alkene/alkybe/alkoxy/alkoxyalkyl/alkoxyalkenyl and alkoxyalkynyl chains (C1-C16), where $R_2$ = Azide. alkyne, biotinylated alkyne<br>4. Y = a ligand (e.g., a letradentate ligand as in DOTA or NOTA or PnAO. but not limited to these ligands) containing an axide or alkyne substituent linked, with or without a Linker 'L', to the bioreductive drugs BA; a ligand that may be coordinated to a metal prior to coupling with BA, or afterwards:<br>S. L = a linker cyclic or acyclic with upto C8 chain |

Examples of this claim include DOTA class of compounds conjugated to azomycin nucleoside and benzotriazene-1,4-dioxides as representatives. Syntheses of two members of these classes are described.

Class III: Macrocyclic Ligands-Conjugated-Bioreductively-Activated Drugs

As an example under this class of drugs, coupling of azido-AZA with an alkynylated DOTA macromolecule is shown in the scheme below.

Scheme 9. Synthesis route for the compounds described with the General Formula 2, Exemplified by the coupling of alkynylated DOTA macromolecule and azido-AZA macromolecule (12)

For Example:

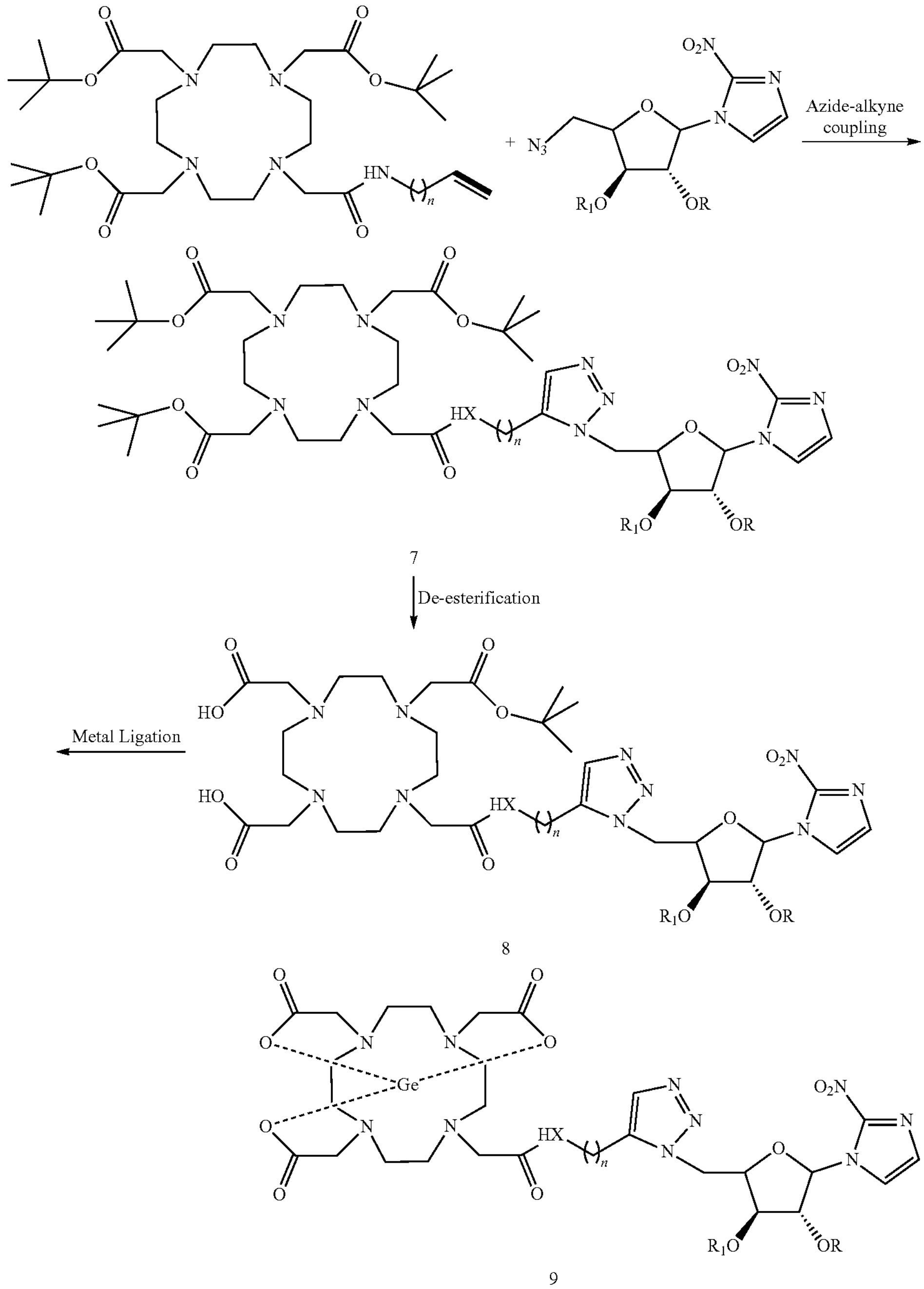

7

8

9

R = H, alkyl, alkenyl, alkynyl estors SR, $SO_2R$, but not limited to $R_1$ = R or either of these Reagents and conditions: (i) Azide-alkyne coupling; (ii) 2 eq. of NaOH, THF, 2 h, Acidification with 1M HCl (iii) Metal coordination exemplified by $GaCl_3$, 0.1M Sodium acetate buffer (pH~5.0), 100° C., 1 h.

Scheme 9. Synthesis Route for the Compounds Described with the General Formula 2; Exemplified by the Coupling of Alkynylated DOTA Macromolecule and Azido-AZA Macromolecule (12)

Example 1: Synthesis of 5'-deoxy-5'-([4-(2,2',2''-(10-(2-(but-3-yn-1-ylamino)-2-oxoethyl)-1,4,7,10-tetraazacyclododecane-1,4,7-triyl)triacetic acid)-1,2,3, -triazolo]-AZA (DOTA-Triazolo-AZA; Compound 8) by the coupling of alkynylated DOTA macromolecule and azido-AZA molecule To the stirred solution of 2,2',2''-(10-(2-(but-3-yn-1-ylamino)-2-oxoethyl)-1,4,7,10-tetraazacyclododecane-1,4,7-triyl)triacetic acid (0.016 g, 0.03 mmol, 1.2 eq), and (3S,4R)-2-(azidomethyl)-5-(2-nitro-1H-imidazol-1-yl)tetrahydrofuran-3,4-diol, 1 (Azido-AZA, 0.010 g, 0.03 mmol, 1 eq) in tert. Butanol, copper sulphate ($CuSO_4$ $5H_2O$, 0.002 g, 0.01 mmol, 0.5 eq) and sodium ascorbate (0.008 g, 0.04 mmol, 1.1 eq) in water were added to the above mixture and allowed to stir at room temperature (22° C.) for 5 h. The reaction progress was monitored by thin layer chromatography. The crude product was purified by silica-gel column chromatography using DCM and MeOH in 8:2 ratio as an eluent to obtain the desired compound 8 as a light yellow solid (yield: 34%). Identity of purified product was confirmed by various spectroscopic analyses provided here. $^1$H NMR (400 MHz, $D_2O$) δ 7.59 (s 1H), 7.17 (s, 2H), 6.29 (s, 1H), 4.51-4.49 (t, J=7.19 Hz, 1H), 4.75-4.73 (t, J=7.19 Hz, 1H), 3.96-3.94 (m, 2H), 3.72-3.69 (m, 2H) 3.43-3.41 (t, J =6.92 Hz, 2H), 3.30 (s, 8H), 2.09-2.05 (m, 2H), 2.46-2.41 (m, 18H); $^{13}$C NMR (100 MHz, $D_2O$) δ177.41, 170.74, 154.67, 130.76, 129.92, 129.25, 122.90, 92.07, 89.21, 77.04, 72.94, 60.50, 59.51, 55.94, 55.52, 54.67, 39.63, 29.04, 28.73; HRMS (ESI$^+$), $(M+H)^+$ calcd. for $C_{29}H_{46}N_{11}O_{12}$, 740.3327; found, 740.3315.

Class IV—Radiopharmaceuticals and their Compositions

General formula 4 for radioligand-based radiopharmaceuticals. Examples of this class of radiopharmaceuticals include where the molecules are chelated with an imaging or radiotherapeutic metal e.g., $^{99}$mTc, Ga-68, Lu-177, Re-186 etc., but not limited to these metals.

Scheme 10.
General Formula 4 - Schematic and the radiolabeling processes for Compounds belonging to Class IV

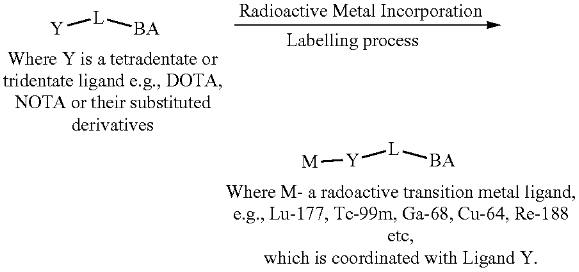

Selected representatives from this class of compounds are described below.

$^{nat}$GaIII complexes of DOTA-TPZ derivative. 1 mmol/0.5 mL (pH 3.0) aqueous solution of the DOTA-TPZ derivative and $Ga(NO_3)_3$ was mixed in a 5-mL vial and heated at 95 □C for 10 min in a water bath. Formation of the Galli complex was confirmed by mass spectrometry. $^{nat}$Ga-DOTA-TPZ: HR-Mass spectrum (ESI+), $(M)^+$ calcd for $C_{25}H_{34}GaN_8O_9$, 659.1705; found, 659.1701.

$^{nat}$LuIII complexes of DOTA-TPZ derivative. 1 mmol/0.5 mL (pH 3.0) aqueous solution of the DOTA-TPZ derivative and $LuCl_3$ was mixed in a 5-mL vial and heated at 95 □C for 15 min in a water bath. Formation of the LuIII complex was confirmed by mass spectrometry. natLu-DOTA-TPZ: HR-Mass spectrum (ESI+), $(M)^+$ Radiosynthesis of $^{177}$Lu-DOTA-TPZ is described as a representative example of this claim.

Figure 11:
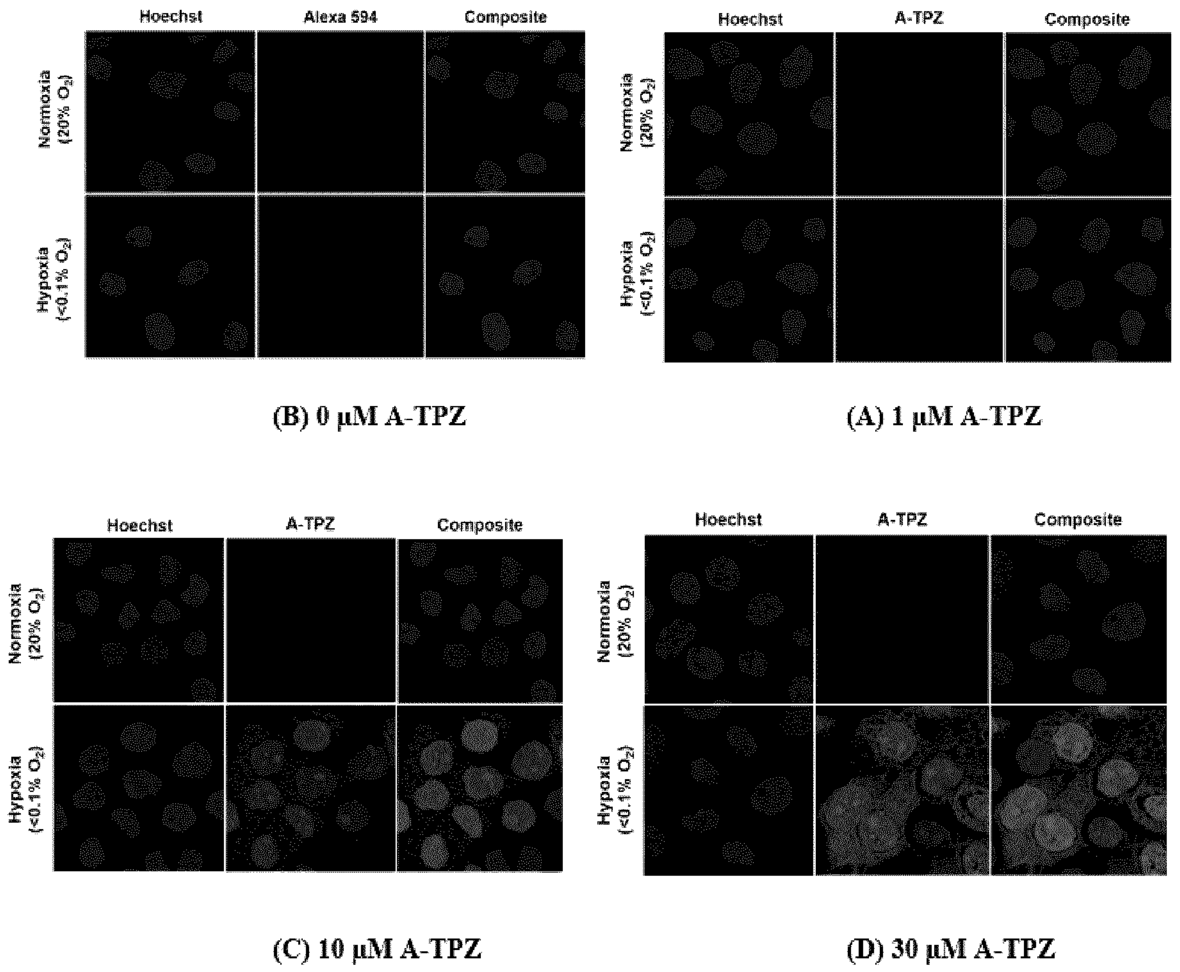
FIG. 11 A-D shows that A-TPZ Click chemistry demonstrates hypoxia-selective mapping potential, which is dose-dependent.

Synthesis of $^{177}$Lu-labelled DOTA-TPZ. $^{177}$Lu was added to the mixture of synthesized (100 nmol) ligand and 0.2 mL of 1 M sodium acetate buffer (pH~5.0) and heated at 95 □C for 15 min in an aluminum heating block (FIG. 11). After completion of the labeling, radiolabeled mixture were passed through the alumina N— light cartridge (prewashed with 10 mL of water) and the cartridge is washed with 1 mL saline. The labeled product was collected and analyzed for radiochemical purity by ITLC-SG/0.1M $Na_2CO_3$ buffer (FIG. 1). Free $^{177}$Lu+ remained at the origin and labeled product moved with the solvent front.

Scheme 11. Radiosynthesis of $^{177}$Lu-labelled DOTA-TPZ molecule

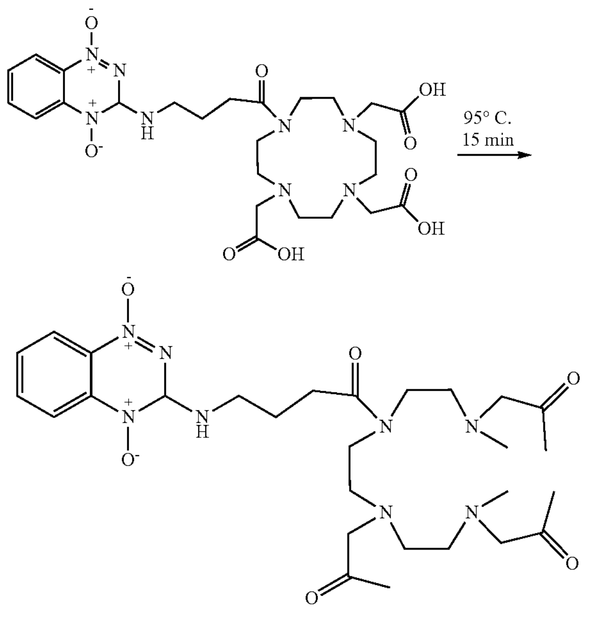

Figure Depicts Radiochromatograms of $^{177}$Lu-DOTA-TPZ Pre- (A) and Post-Purification (B)

Stability Evaluation of $^{177}$Lu-Labelled DOTA-TPZ Pre- (Left) and Post-Purification (Right)

Stability of $^{177}$Lu-DOTA-TPZ: Evaluation of the $^{177}$Lu-DOTA-TPZ revealed that the product stays >95% pure and stable for up to 24 h under normal storage conditions (22° C.; See FIG. 2), legitimating its suitability for the proposed therapeutic use.

Figure 2:
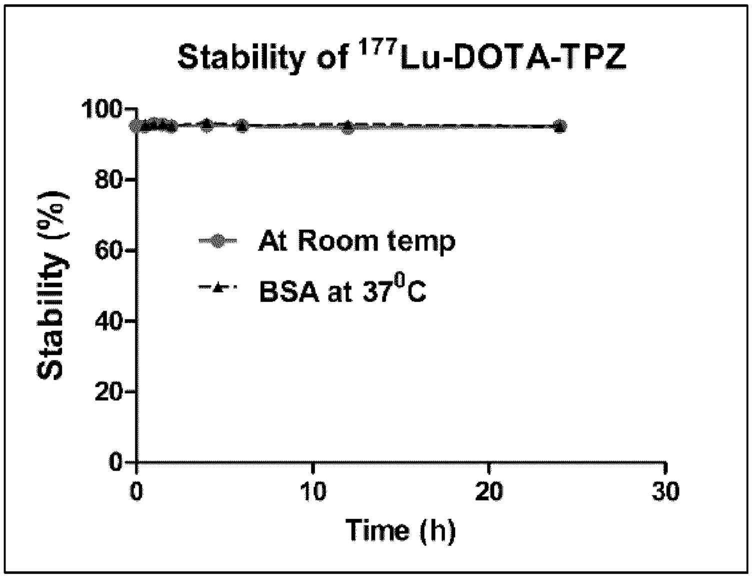
FIG. 2 depicts the stability of radioactive compounds of Class IV as exemplified by radioactive $^{177}$Lu-labelled DOTA-TPZ FIG. 3 A-D depicts hypoxia-selective sensitization of ACN in FaDu cells FIG. 4 A-D depicts inverse oxygen dependent entrapment of Azido-AZA (ACN)—ACN click chemistry on fixed FaDu cells treated with either DMSO (A) or different concentrations (1 μM, 10 μM or 100 μM) of ACN (B-D) demonstrated that the fluorescent signal is only present in oxygen deprived cells. The signal was most concentrated in anoxic samples, and 100 μM ACN treated samples showed the most pronounced differences. Hoechst nuclear staining is shown in blue and the click chemistry reaction in green. Scale bar represents 20 μm.

FIG. 2 depicts stability studies of $^{177}$Lu-DOTA-TPZ in prepared medium, in human serum and bovine serum albumin.

Partition Coefficient determination of $^{177}$Lu-DOTA-TPZ: $Na_2HPO_4$ buffer (0.1 M, pH 7.4, 3 g) was added to octanol (3 g), and then $^{177}$Lu-DOTA-TPZ (74 kBq/2 μL) was added, mixed vigorously, and centrifuged (3,000 rpm for 5 min). The radioactivities in the octanol fraction (0.5 g) and the 0.1 M $Na_2HPO_4$ buffer fraction (0.5 g) were measured using a γ-scintillation counter, and log P values were calculated (Table 1).

Measurement of Serum Protein Binding of $^{177}$Lu-DOTA-TPZ: Human serum protein binding assays were performed with $^{177}$Lu-DOTA-TPZ. PD-10 columns were preconditioned by loading 1.0 mL of 1% bovine serum albumin in 0.1 M diethylene triamine pentaacetic acid (DTPA) and eluted with 10 mL of phosphate buffered saline (PBS). $^{177}$Lu-DOTA-TPZ (0.37 MBq/50 μL) was mixed with human serum (0.5 mL) and incubated for 10 min and 60 min at 37 □C. Each mixture (0.074 MBq/100 μL) was loaded onto a preconditioned PD-10 column and eluted with PBS; 30 fractions (fraction size=0.5 mL) were collected per sample in 5-mL test tubes. The radioactivity of each fraction was measured using a γ-scintillation counter and expressed as cpm (counts per minute). To verify the presence of protein in each fraction, an aliquot (2 μL) from each test tube was spotted on a filter paper and stained with Coomassie blue. Percentage binding of $^{177}$Lu-DOTA-TPZ to protein were calculated using fraction activity curves. Data related to partition coefficient (log P), percent protein binding, radiochemical yield and the specific activity are summarized below in Table 1.

TABLE 1

Partition Coefficient, Protein Binding, Radiochemical Yield, and Specific Activity of the radiolabeled $^{177}$Lu-DOTA-TPZ[a]

| Compound | Partition coefficient (log P) | Protein binding (%) 10 min | Protein binding (%) 60 min | Radio-chemical yield (%) | Specific activity (GBq/μmol) |
|---|---|---|---|---|---|
| $^{177}$Lu-DOTA-TPZ | −2.39 ± 0.17 | 0.72 ± 0.23 | 1.20 ± 0.26 | 95.4 ± 1.24 | 5.33 ± 0.74 |

[a]The values represent mean ± SD (n = 4).

MRT, Chemosensitization Therapy, Radiosensitization Therapy, Auger Therapy, PDT Therapy, Acoustic Therapy, Hypoxia Imaging (a). Molecular imaging including fluorescence, optical, MRI, radioactive PET and SPECT and other modes facilitated by the compounds herein (PET imaging for example using F-18, I-124, Ga-68 and SPECT for example using e.g., I-131 and I-123, optical imaging using fluorescent dyes); therapeutic uses include chemotherapy (e.g., I-127, F-19-, and other non-radioactive compounds); Auger Therapy (I-125), photo-dynamic therapy (PDT), radiosensitization, acoustic imaging, and Molecular Radiotherapy [MRT; I-131, Lu-177, Re-186 but not limited to these isotopes]) of the molecules described in claims 1-4, and the related processes;

(b). Theranostic uses (PET and SPECT imaging, MRI, fluorescence, optical, PDT, radiosensitization, MRT) of the molecules described above and the related processes and benefits.

Biological Studies

In vitro cell culture-based and in vivo tumor-bearing animal model-based hypoxia mapping studies have been performed using representative molecules from the claims. The studies and the findings related to "click mapping" are described below.

Cell Culture

Human head and neck squamous cell carcinoma cell line, FaDu, was purchased from American Type Culture Collection (ATCC HTB-43). FaDu cells were cultured in Dulbecco's Modified Eagle's medium/Nutrient Mixture F-12 media supplemented with 10% Fetal bovine serum, 2 mM L-glutamine and 10% Penicillin Streptomycin. Cells were cultured in a humidified incubator at 37° C. with 5% $CO_2$.

1. Evaluations of ACN

Evaluation of Hypoxic Cytotoxicity and Radiosensitization Potential of ACN

Hypoxic cytotoxicity of ACN was evaluated using colony formation assay. FaDu cells were seeded on 60 mm glass petri dishes (in triplicates) at a density of 300 cells per plate. Cells were allowed to attach for 24 hours, followed by treatment with 1 μM, 10 μM and 100 μM of freshly dissolved ACN for 24 hours under normoxia (20% $O_2$) or hypoxia (1% $O_2$ and <0.1% $O_2$); 100 μM DMSO was used as vehicle control. Cells were allowed to grow and form colonies for 14 days. Colonies were stained with crystal violet, counted and plotted as percentage of vehicle conditions; error bars show standard error of the means. To assess the radiosensitization potential of ACN, FaDu cells seeded on 60 mm glass dishes (in triplicates, at densities ranging from 300 to 900 cells per plate) were allowed to attach for 24 hours, followed by treatment with 100 μM of ACN or DMSO for 24 hours under normoxia or hypoxia (<0.1% $O_2$). Afterwards, one set of plates for each $O_2$ condition was irradiated (5 Gy). 1 hr post IR (ionizing radiation), hypoxic cells were re-oxygenated, media was replaced for all plates, cells were allowed to grow and form colonies for 14 days. Colonies were stained with crystal violet, counted and plotted as percentage of vehicle (DMSO) controls; error bars represent standard error of the means. To test if ACN affects cell proliferation, ~0.8 million FaDu cells seeded on 60 mm glass petri dishes were allowed to attach for 24 hours, treated with 100 μM of ACN or DMSO and incubated under normoxia and hypoxia (<0.1% $O_2$) for 24 hours. Afterwards, one set of plates for each $O_2$ condition was irradiated (5 Gy). 1 hr following IR, cells were trypsinized, counted, and seeded on 24 well plates in triplicates at a density of 50,000 cells per well. Cells were trypsinized 1, 3, 5 and 7 days after re-plating, and counted with a Z2 coulter particle counter.

Evaluation of In Situ Hypoxia Mapping Potential of ACN: Click Chemistry Reaction Click Chemistry Reaction The Click-IT reaction cocktail (Molecular Probes) was made up according to the manufacturer's directions using a 1:5000 dilution of the 2 mg/ml Alexafluor 555 or 594 conjugated alkyne stock (Molecular Probes). The reaction cocktail was used within 15 minutes of preparation. All reactions were done at room temperature in the dark.

In Vitro Validation of Inverse Oxygen Dependent Entrapment of Azido AZA (ACN)

Subconfluent FaDu cells were trypsinized, and approximately 3-5×$10^5$ cells were seeded in 35 mm tissue culture plates containing sterilized 18 cm×18 cm glass coverslips. Cells were allowed to grow overnight, and treated with different concentrations of ACN (1 μM, 10 μM and 100 μM) under normoxia (20% Oxygen), hypoxia (1% Oxygen) or anoxia (0% Oxygen) for 6 hours. Hypoxia and anoxia were achieved using an in house de-gassing system. Post-treatment, all steps were carried out at room temperature. Cells were washed three to five times with 1×PBS, fixed in 2% paraformaldehyde (PFA) for 20 minutes, and washed again three times with 1×PBS. The fixed cells were then blocked and permeabilized with 1% BSA in 1×PBS containing 0.1% Triton-100 for 20 minutes, followed by incubation with click cocktail containing Alexafluor 594 conjugated alkyne for 30 minutes. Subsequently cells were washed and stained with Hoechst 33342 (1:10000 dilution in PBS, Life Technologies) for 5 minutes before mounting them on glass slides (Fluoroshield Mounting Medium, abcam). The prepared slides were kept at 4° C. until imaged. Images were obtained by with a Plan-Apochromat 40X/1.3 Oil DIC lens on a Zeiss 710 confocal microscope using Zen 2011 software.

Comparison Between Hypoxia Selective Uptake of ACN and Pimonidazole In Vitro

FaDu cells were grown on coverslips (as described above) and treated simultaneously with 100 μM ACN and 100 μM Pimonidazole. The cells were subsequently exposed to normoxic (20% Oxygen), hypoxic (1% Oxygen) or anoxic (0% Oxygen) conditions for 6 hours, and fixed in 2% PFA. Standard Pimonidazole IHC was performed as described elsewhere using an Alexafluor 647 labelled secondary antibody. Click chemistry was performed as previously described using an Alexafluor 555 conjugated alkyne followed by nuclear staining with Hoechst. Mounted coverslips on glass slides were imaged as described earlier.

Retention Profile of ACN in Hypoxic Cells Following Re-Oxygenation:

After bioreductive activation under hypoxia, nitroimidazole reactive species (nitroradical anion) bind to cellular nucleophiles to form drug-protein adducts. To evaluate how fast these adducts are metabolized, we treated FaDu cells with 100 μM of ACN under normoxia or anoxia for 6 hours, and exposed them to subsequent re-oxygenation. Cells were fixed after 0 hr, 1 hr, 3 hr, 6 hr and 18 hr of re-oxygenation. Click chemistry was performed on fixed cells as previously described.

Assessment of ACN as a Hypoxia Tracer

Female BALB/c nude mice (Charles River Laboratories) aged 6 weeks were used and cared for according to the CCAC guidelines. We used a biflanked sub-cutaneous tumor model where the tumor in the left flank was untreated (control) and the tumor in the right flank served as the 'treatment' group. We subcutaneously injected $6\times10^6$ FaDu cells in 0.1 ml of sterile 0.9% NaCl into the upper right flank to form palpable tumors. The tumors were measured daily until the volume reached 10 mm3. The mice were divided into 4 groups and injected intraperitoneally in 0.15 ml 0.9% saline with: 1-80 mg/Kg ACN, 2-80 mg/Kg pimonidazole (Hypoxyprobe), 3-80 mg/Kg ACN:pimonidazole in a 1:1 ratio and 4-0.9% saline control. Mice were sacrificed 2 hours post-injection, tumors removed and frozen in OCT. Seven micron serial sections were taken of each tumor, dried and stored at −80° C.

Assessment of ATZ as a Hypoxia Tracer

Tirapazamine was assessed following the same protocol as above for ACN, but using ATZ at 60 mg/Kg in place of ACN. Animals were sacrificed 2, 4 and 18 hours post-injection.

Immunofluorescence and Click Chemistry

Tissue sections were air dried for 25 minutes, fixed for 5 minutes in −20° C. acetone; air dried 25 minutes and blocked in PBS with 1% BSA for 20 minutes. Sections were incubated with primary antibodies for small vessel endothelium [1:100 rabbit anti-CD34 (abcam)] or hypoxia [1:100 rabbit anti-pimonidazole Hypoxyprobe)] for 2 hours at room temperature, followed by 3 five minute washes in 1×PBS. The secondary antibody (Alexafluor 647 goat anti-rabbit 1:1000 Molecular Probes with 1×DAPI to stain DNA) was incubated for 30 minutes at 37° C. at room temperature in the dark, followed by 3 five minute washes with 1×PBS. The Click-IT reaction cocktail was incubated with the sections for 30 minutes. Sections were washed 5 times with 1×PBS for 5 minutes and mounted using Mowiol 4-88 (Calbiochem) mounting media. Slides were stored at 4° C. until imaged. Images were obtained by tile scan with a Plan-Apochromat 10X/0.45 numerical aperture lens on a Zeiss 710 confocal microscope using Zen 2011 software. Scale bars were added to the images using Adobe Photoshop.

In Vivo Evaluation of Radiosensitization Therapy by IAZA using "Click Mapping"

Male Nu/Nu mice (Charles River Laboratories) aged 6 weeks were used and cared for according to the CCAC guidelines. FaDu cells were cultured in Dulbecco's Modified Eagle's medium/F-12 media supplemented with 10% Fetal bovine serum and 2 mM L-glutamine. We subcutaneously injected $8\times10^6$ FaDu cells in 0.1 ml of sterile 0.9% NaCl into both flanks to form bilateral palpable tumors. The tumors were measured daily until the volume reached 0.4 cm3. Mice were anesthetized with isoflurane for a pre-therapy MRI scan, including intravenous injection of 0.3 mmol/Kg of Gadovist contrast agent (Bayer) using an in house 9.4 Tesla animal MRI scanner. Body temperature was maintained under anesthesia in the MR bore using warm air (MR-compatible Small animal Heating System, SA Instruments Inc.). Temperature and respiration were monitored and recorded every five minutes throughout the scans (Small animal Monitoring and Gating System, SA Instruments Inc.). The next day, animals were injected intraperitoneally with either 400 mg/Kg IAZA (20% maximum tolerated dose) or 5% DMSO in 0.15 ml sterile 0.9% saline. Four to six hours later, each mouse was anesthetized with isoflurane and placed in the Small Animal Radiation Research Platform (Xstrahl Life Sciences). A CT scan was obtained of the right tumor using SSARP GUI software, registered and refined using MuriSlice software. The CT images were loaded into MuriPlan software to create and execute a treatment plan to deliver a single dose of 10 Gy radiation (RT) to the right tumor of each mouse. The left tumor served as the unirradiated internal control for each mouse. Animals were monitored and tumors measured for up to 16 days. A mid-therapy MRI was performed 48 hours post-RT and the post-therapy MRI was performed when the unirradiated tumor (left) reached 1 $cm^3$. Mice were injected intraperitoneally in 0.15 ml 0.9% saline with 60 mg/Kg ACN 24 hours after the post-therapy MRI scan. Mice were sacrificed 2 hours post-injection, tumors removed and frozen in OCT. Seven micron serial sections were taken of each tumor, dried and stored at −80° C.

Results

ACN Displays No Hypoxia-Selective Sensitization in FaDu Cells

In colony formation assays, ACN (at concentrations up to 100 μM) did not show any hypoxia-selective cytotoxicity (FIG. 3A). No hypoxic radiosensitization was observed when FaDu cells were treated with a combination of 100 μM ACN and 5 Gy IR (FIG. 3B). In cell proliferation assays, ACN treatment alone or in combination with 5 Gy IR did not generate significant difference in cell counts compared to vehicle (DMSO or DMSO+IR respectively) control (FIG. 3C and 3D).

Figure 3:
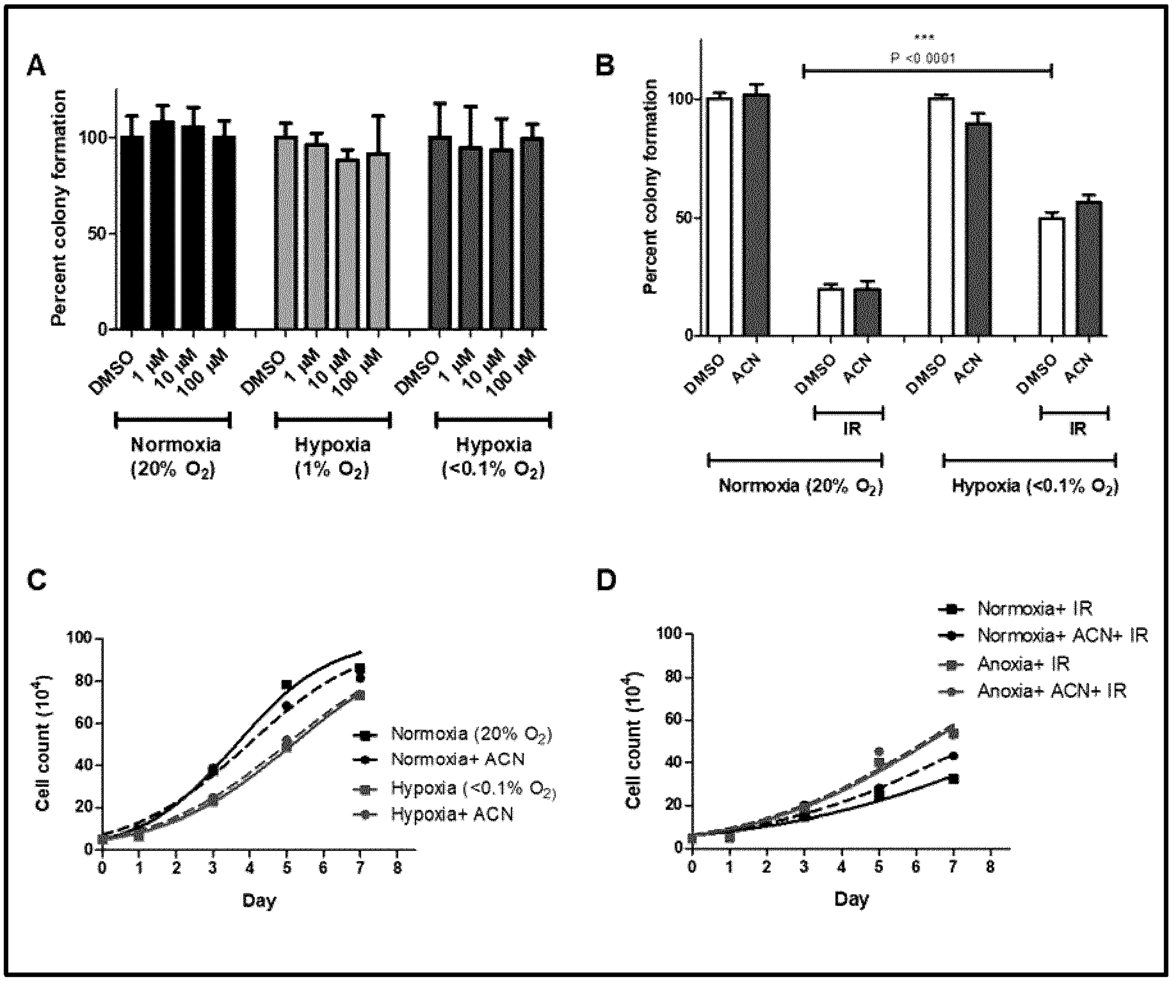

FIG. 3 depicts ACN displayed no hypoxia selective sensitization-ACN treatment did not affect clonogenic potential of normoxic (20% $O_2$) or hypoxic (1% $O_2$ and <0.1% $O_2$) FaDu cells (A). Hypoxic FaDu cells showed significant resistance to IR; however, no hypoxic radiosensitization was observed when FaDu cells were treated with 100 μM ACN in combination with 5 Gy IR (B). ACN treatment alone (C) or in combination with 5 Gy IR (D) did not alter FaDu cell proliferation.

ACN Click Chemistry is Selective for Oxygen-Deprived Cells

Our test compound, ACN, was entrapped in FaDu cells in an inverse oxygen dependent manner, where the highest retention was observed under <0.1% $O_2$. Well oxygenated or normoxic cells showed minimal to almost no entrapment (FIG. 4A-D). Click chemistry between the azide moiety of ACN and the fluorophore conjugated alkyne enabled us to identify the hypoxia selective entrapment of the compound using fluorescence microscopy. ACN was also entrapped in hypoxic cells in a dose dependent manner, with 100 μM concentration demonstrating the most vivid differences (FIG. 4D).

In oxygen-deprived cells treated with ACN, we saw structures that resembled endoplasmic reticulum staining, however this needs further validation. In lower dose treated cells, we saw possible nucleolar localization of ACN.

Figure 4:
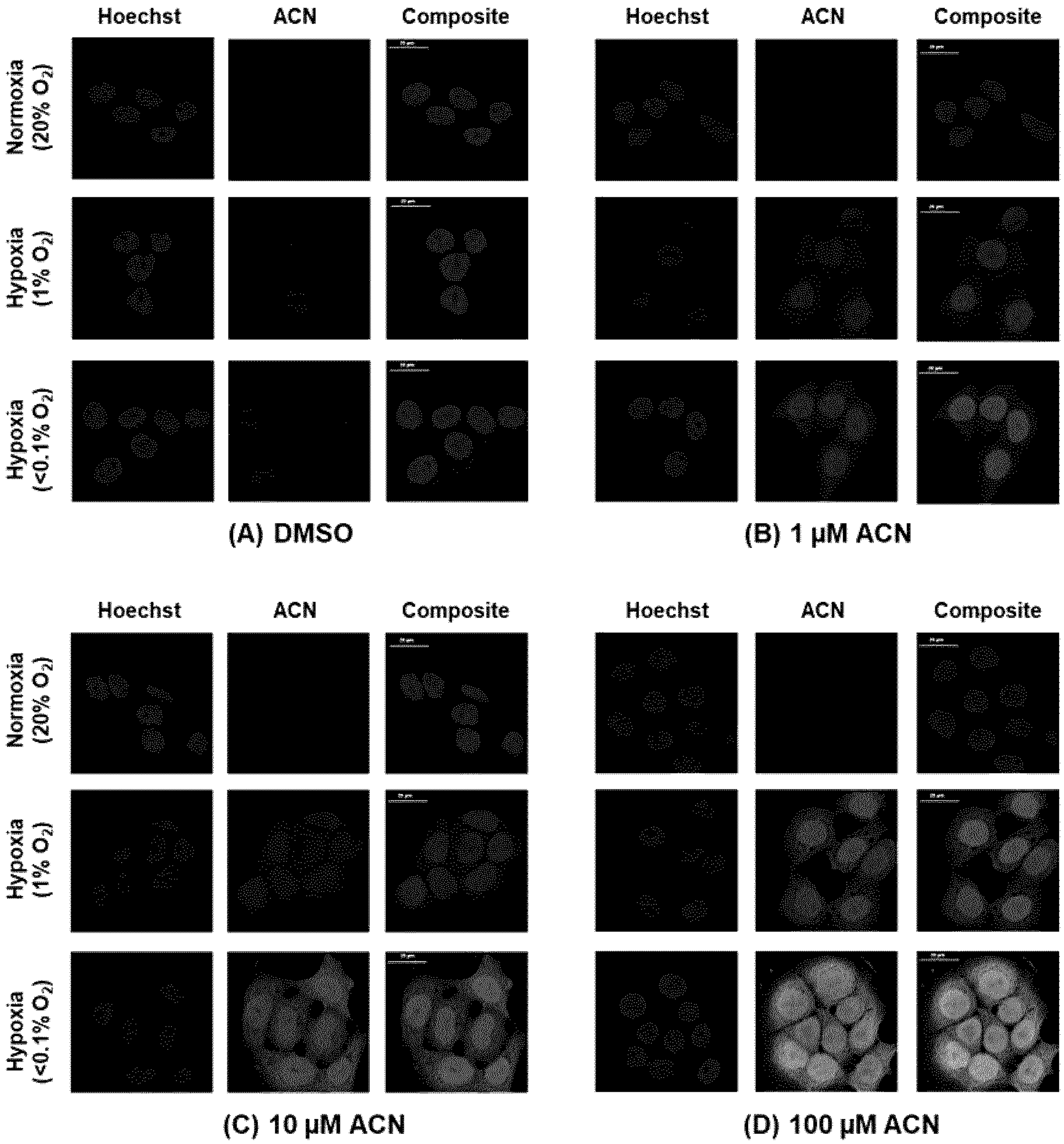

FIG. 4 depicts inverse oxygen dependent entrapment of ACN-ACN click chemistry on fixed FaDu cells treated with either DMSO (A) or different concentrations (1 μM, 10 μM or 100 μM) of ACN (B-D) demonstrated that the fluorescent signal is only present in oxygen deprived cells. The highest click signal was seen in hypoxic (<0.1% $O_2$) 100 μM ACN treated cells. Normoxic ACN treated cells displayed minimal to no background signal, even at highest drug concentrations. Hoechst nuclear staining is shown in blue and the click chemistry reaction in green. Scale bar represents 20 μm.

Figure 5:
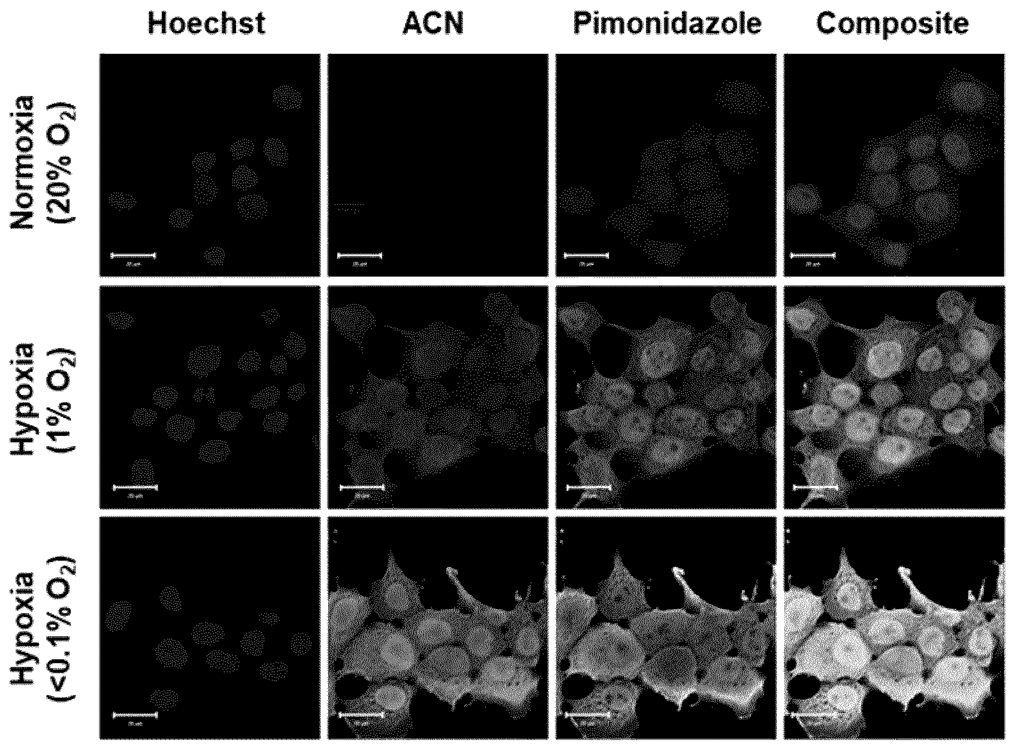
FIG. 5. Comparison between hypoxia selective uptake of ACN and Pimonidazole—Immunofluorescence studies with FaDu cells treated with both ACN and Pimonidazole (100 μM of each compound) illustrated that both ACN and Pimonidazole can be detected in oxygen deprived cells. Anoxic samples showed higher nuclear staining for ACN whereas the Pimonidazole signal was mostly concentrated in the cytoplasm. Hoechst nuclear staining is shown in blue, the click chemistry reaction in green and the Pimonidazole immunostaining in red. Scale bar represents 20 μm.

ACN and Pimonidazole Staining Indicates Possible Co-Localization in Hypoxic Cells:

Both ACN click chemistry and Pimonidazole immunofluorescence staining was detected in oxygen deprived cells, with minimal signal in normoxic samples (FIG. 5). ACN showed higher nuclear signal in hypoxic <0.1% $O_2$ cells, whereas Pimonidazole staining was mostly concentrated in the cytoplasm.

FIG. 5 depicts comparison between hypoxia selective uptake of ACN and Pimonidazole—Immunofluorescence studies with FaDu cells treated with both ACN and Pimonidazole (100 μM of each compound) illustrated that both ACN and Pimonidazole can be detected in oxygen deprived cells. Hypoxic (<0.1% $O_2$) samples showed higher nuclear staining for ACN whereas the Pimonidazole signal was mostly concentrated in the cytoplasm. Hoechst nuclear staining is shown in blue, the click chemistry reaction in green and the Pimonidazole immunostaining in yellow. Scale bar represents 20 μm.

ACN-Protein Adducts in Hypoxic Cells could be Detected Up to 24 Hours Following Normoxic Exposure:

In FaDu cells subjected to re-oxygenation following hypoxia, the fluorescent signal for ACN-protein adducts gradually faded over time (FIG. 6B). The signal could be detected up to 6 hours after re-oxygenation, however very faint signal was observed in samples that underwent 18 hours re-oxygenation. Minimal background was seen in their normoxic counterparts (FIG. 6A).

Figure 6:
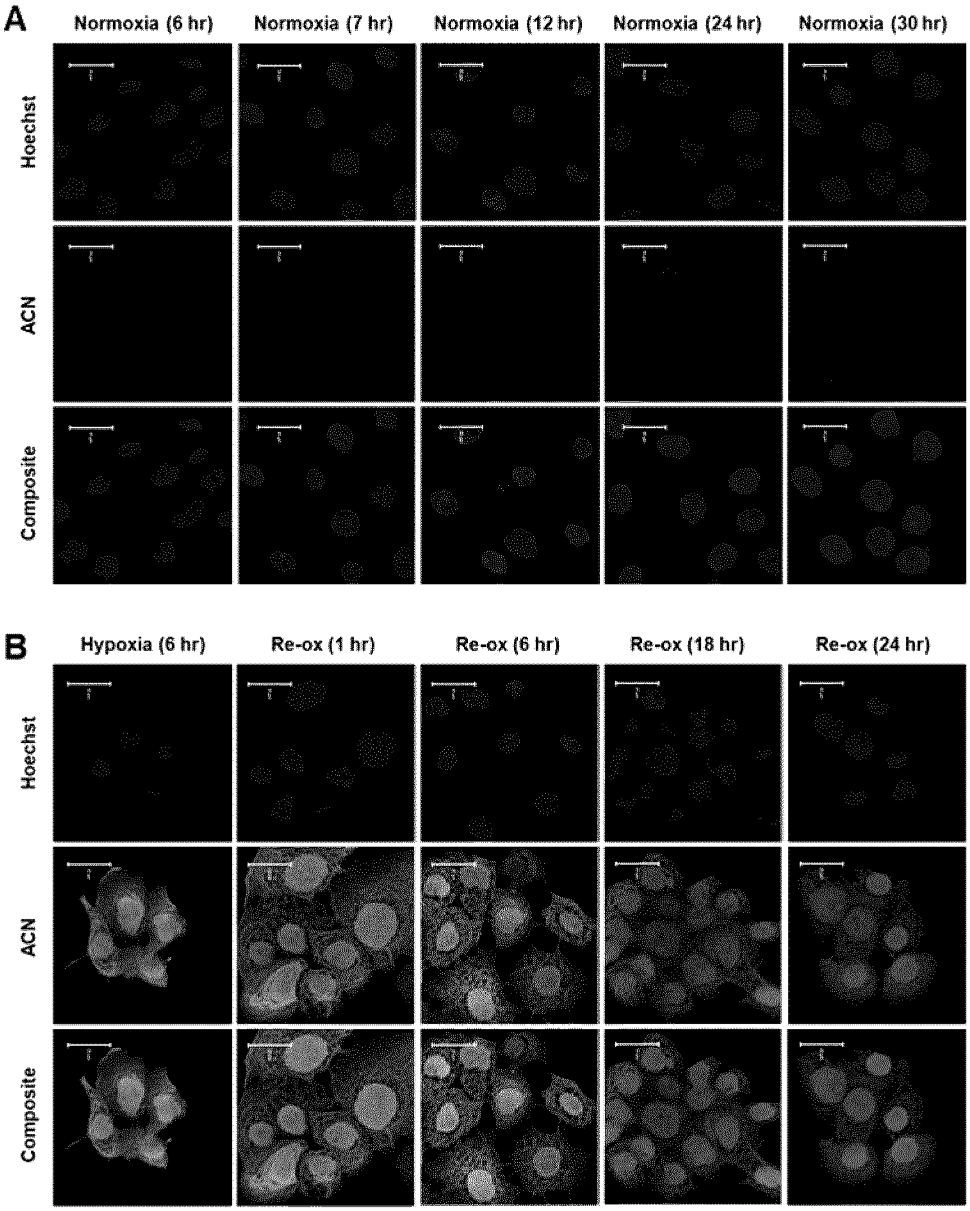
FIG. 6. Retention profile of Azido AZA (ACN) in hypoxic cells following re-oxygenation—ACN click chemistry signal in ACN treated FaDu cells decreased over time when the cells were subjected to re-oxygenation after 6 hours of anoxia (B); the click signal could be detected up to 6 h after re-oxygenation and finally faded almost to background after 18 h of re-oxygenation. The normoxic counterparts showed minimal background (A). Hoechst nuclear staining is shown in blue and the click chemistry reaction in green. Scale bar represents 20 μm.

FIG. 6 depicts retention profile of Azido AZA (ACN) in hypoxic cells following reoxygenation—ACN click chemistry signal in ACN treated FaDu cells could be detected up to 24 hours after re-oxygenation (B). The normoxic counterparts showed minimal background (A). Hoechst nuclear staining is shown in blue and the click chemistry reaction in green. Scale bar represents 20 μm.

Assessment of ACN as a Hypoxia Tracer

Figure 7:
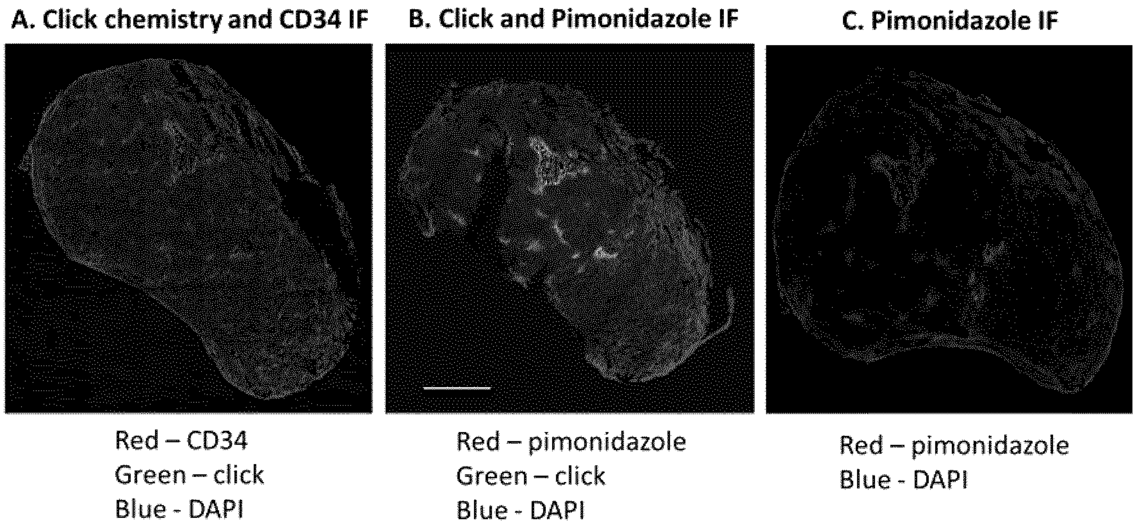
FIG. 7. Click chemistry defines hypoxic regions of tumors—7 micron serial tumor sections of the ACN: Pimonidazole 1:1 injected animal illustrated that the click chemistry reaction defines the regions of hypoxia and co-localizes with the known hypoxia marker pimonidazole. DAPI is shown in blue and the click chemistry reaction in green. Red represents the vasculature in (A) and pimonidazole immunostaining in (B) and (C). Scale bar represents 1 mm.

Regions of tumor hypoxia defined by the click chemistry reaction are present bordering areas of necrosis and are independent of the vasculature (FIG. 7A). Similar results were seen for pimonidazole and Hoechst33342 in FaDu xenografts (McCall et al., Int. J. Radiat. Oncol. Biol. Phys. 2012 84:393-399) Pimonidazole immunostaining and the click chemistry do co-localize to hypoxic areas bordering necrotic regions as expected (FIG. 7B). In addition, click chemistry offers the advantage of a single step rapid detection of hypoxia. Pimonidazole immunostaining is identical in the absence of click chemistry indicating that the click chemistry reaction does not interfere with the immunostaining (FIGS. 7B and C). There is non-specific staining of the tissues immediately surrounding the tumor by the secondary antibody used for pimonidazole and CD34 (FIG. 7). This again illustrates the advantage of the click chemistry.

In summary, our compound, ACN, co-localizes in hypoxic regions of FaDu xenograft tumors with the currently used hypoxyprobe, pimonidazole, but not the vascular marker CD34. Click chemistry has the following advantages over immunostaining: specific, rapid (only 30 minutes), single step and no non-specific staining.

FIG. 7 depicts click chemistry defines hypoxic regions of tumors-7 micron serial tumor sections of the ACN: Pimonidazole 1:1 injected animal illustrated that the click chemistry reaction defines the regions of hypoxia and co-localizes with the known hypoxia marker pimonidazole. DAPI is shown in blue and the click chemistry reaction in green. Red represents the vasculature in (A) and pimonidazole immunostaining in (B) and (C). Scale bar represents 1 mm.

ACN-Based Imaging Study of IAZA as a Radiosensitzer

Figure 8:
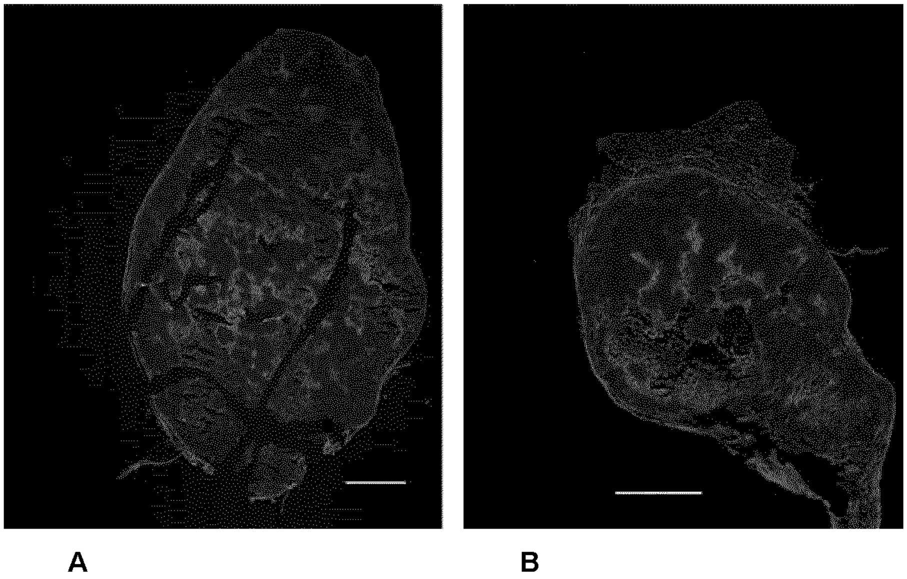
FIG. 8. Evaluation of hypoxic region by ACN mapping in a control (A) and radiation (B) (10 Gy) treated FaDu tumor bearing mouse—7 micron serial sections of the left (DMSO control) and right (single dose of 10 Gy radiation) tumors of the same animal illustrated that radiation shrank the tumor but did not affect tumor hypoxia. DAPI is shown in blue and the click chemistry reaction in green and red represents the vasculature. Scale bar represents 1 mm.
Figure 9:
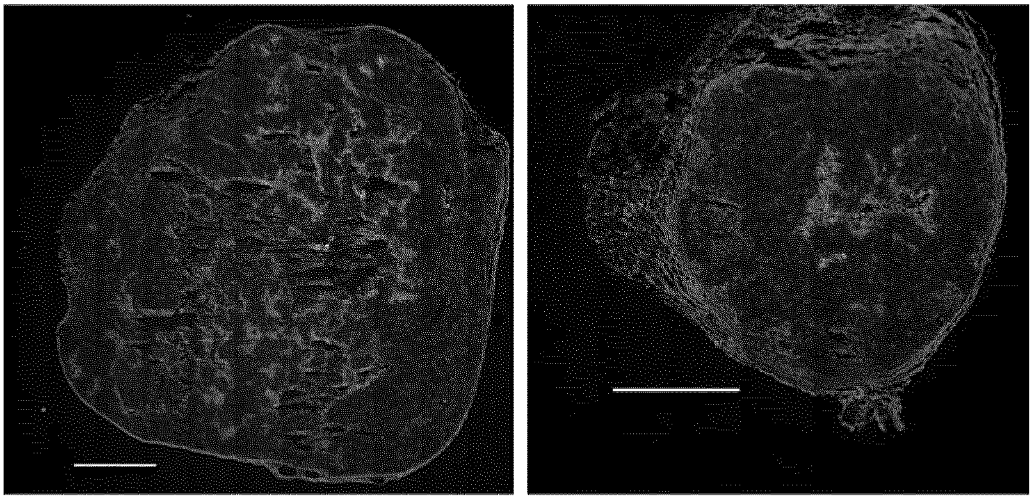
FIG. 9. Evaluation of hypoxic region by ACN mapping after treatment with IAZA alone (A) and IAZA+radiation (B) (10 Gy) in FaDu tumor bearing mouse—Seven micron serial sections of the left (IAZA alone) and right (IAZA+single dose of 10 Gy radiation) tumors of the same animal illustrated that the combination of radiation and IAZA shrank the tumor and reduced the hypoxia. DAPI is shown in blue and the click chemistry reaction in green and red represents the vasculature. Scale bar represents 1 mm. Red—CD34; Green—click, Blue—DAPI.

Radiation therapy caused the tumors to shrink, but did not have an obvious effect on hypoxia within the tumors (FIG. 8). This is expected since hypoxic cells are more radio-resistant and a single dose of 10 Gy is effective in the short term of this study. IAZA alone had no effect on hypoxia as there is no difference between the control tumors and the tumors treated with IAZA only (FIGS. 8 and 9). IAZA has been reported to have low toxicity to human and murine cancer cell lines and is selectively taken up by hypoxic cells, which is in agreement with our finding (Stypinski et al., Nuclear Medicine Communications 1999 20: 559-567). We observed both tumor shrinkage and reduced hypoxia in the IAZA and radiation co-treated tumors (FIG. 9). Although the tumors regressed with the combination of IAZA and radiotherapy, the presence of the control tumor on the same animal did not allow us to follow the tumor to see if the regression could be sustained for any length of time.

FIG. 8 Depicts evaluation of hypoxic region by ACN mapping in a control (A) and radiation (10 Gy) treated FaDu tumor bearing mouse (B)—7 micron serial sections of the left (DMSO control) and right (single dose of 10 Gy radiation) tumors of the same animal illustrated that radiation shrank the tumor but did not affect tumor hypoxia. DAPI is shown in blue and the click chemistry reaction in green and red represents the vasculature. Scale bar represents 1 mm.

FIG. 9 depicts evaluation of hypoxic region by ACN mapping after treatment with IAZA alone (B) and IAZA+radiation (10 Gy) in FaDu tumor bearing mouse (B). Seven micron serial sections of the left (IAZA alone) and right (IAZA+single dose of 10 Gy radiation) tumors of the same animal illustrated that the combination of radiation and IAZA shrank the tumor and reduced the hypoxia (compare FIG. 17 right 'RT alone' tumor image with FIG. 18 right image of tumor section demonstrating 'IAZA+RT [10 Gy] effect). DAPI is shown in blue and the click chemistry reaction in green and red represents the vasculature. Scale bar represents 1 mm. Red—CD34; Green—click, Blue—DAPI 2. Evaluations of A-TPZ Crystal violet staining (CVS) and colony formation assay (CFA) were performed in order to examine the cytotoxicity of A-TPZ, and Click Chemistry was performed to determine hypoxia-selective sub-cellular localization of these bioreductively activated drugs. These methods are described below.

Crystal Violet Staining (CVS) Assay

FaDu cells (3000 cells/well) were seeded on 96-well microtitre plates and were incubated overnight at 37° C. with 5% $CO_2$ to get attached to the surface. Next day, the cells were treated with increasing doses of drug (1-100 μM) and the plates were incubated under normoxic (20% $O_2$) and hypoxic (0.1% $O_2$) conditions for 72 hours. Culture medium (DMEM and low glucose DMEM) without cells was set for background, according to the experimental set up. After the required incubation period, the media was aspirated, and the plates were allowed to dry for a few minutes followed by addition of crystal violet solution for 20 minutes in order to stain the cells. Subsequently, the dye was discarded, plates were washed with water and let to dry overnight. Methanol (150 μL) was added to the wells and incubated for 20 minutes, so as to dissolve the crystals. Absorbance of the samples was measured spectrophotometrically using an ELISA plate reader at a wavelength of 520 nm. The absorbance of background wavelength (media only) was subtracted from the other absorbance results.

Colony Formation Assay

FaDu cells (optimum density—ranging from 300-3000 cells) were seeded on 60 mm plates and were incubated overnight at 37° C. with 5% $CO_2$ to get attached to the surface. The cells were then treated with increasing doses of drug and the plates were incubated under both normoxic (20% $O_2$) and hypoxic (0.5% $O_2$) conditions for 24 hours. The media was changed and the plates were incubated for another 14 days (at 37° C. with 5% $CO_2$) to let the colonies develop. After 14 days, the colonies were stained with crystal violet solution and counted.

Selective Sub-Cellular Localization

FaDu cells (~0.5 million) were seeded on coverslips in 30 mm dishes and were incubated overnight at 37° C. with 5% $CO_2$ to get attached to the surface. Cells were then treated with increasing concentrations (1-30 μM) of drug (reconstituted in DMSO at concentration of 0.5 M) and were incubated under normoxic and hypoxic (<0.1% $O_2$) conditions for 24 hours. Post-treatment, cells were fixed with 2% paraformaldehyde for 20 minutes followed by blocking and permeabilization in 1% BSA and 0.1% Triton-X-100 for 20 minutes. Click reaction was performed in the presence of Alexa 594 alkyne using the Click-iT Cell Reaction Buffer Kit (Thermo Fisher Scientific, no: C10269), according to manufacturer's protocol. Nuclei were counterstained with Hoechst, and images were obtained using confocal microscopy.

Dose-Dependent Hypoxic Selective Cytotoxicity of A-TPZ

Figure 10:
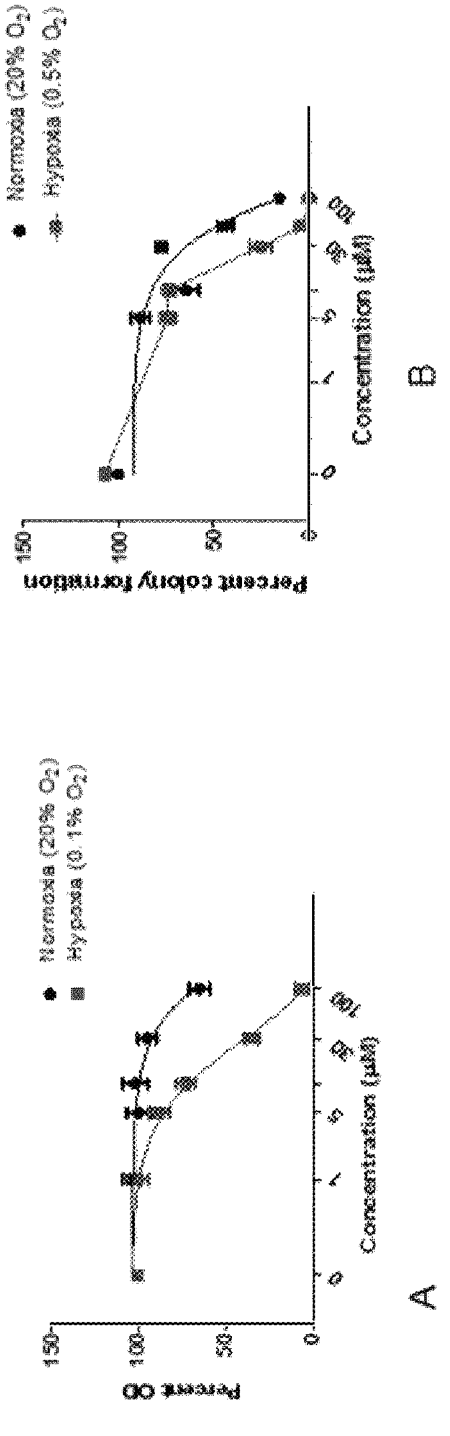
FIG. 10 A&B shows hypoxia-selective toxicity of A-TPZ in FaDu cells.

As shown in FIG. 10 (i), as assessed by CVS assay, A-TPZ showed selective cytotoxicity in low oxygen levels (0.1% $O_2$) and minimal toxicity was observed in the normoxic group. A-TPZ, appeared to be slightly less toxic when compared to the parent compound- TPZ (data not shown). This renders A-TPZ as a good model to study on, since the azide modification, did not seem to drastically alter the toxicity of the parent compound. A similar trend was observed in colony formation assay as well [FIG. 10 (ii)].

FIG. 10 depicts hypoxic selective cytotoxicity of A-TPZ. Cytotoxicity of A-TPZ treated cells as seen with the crystal violet staining assay (CVS) (A) and Colony forming assay (CFA) (B). In CVS assay (i), FaDu cells (3000 cells/well) were seeded on 96 well plates and were incubated overnight to adhere. The cells were then treated with increasing doses of A-TPZ and the plates were exposed to both normoxic (20% $O_2$) and hypoxic (0.1% $O_2$) conditions for 72 hours. Culture medium (DMEM) without cells was set for background. Media was aspirated post-treatment followed by addition of crystal violet solution to stain the cells. Crystals were dissolved using methanol and absorbance of the samples was measured spectrophotometrically. Error bars represent the standard error of the mean. In CFA, (ii), FaDu cells (optimum density-ranging from 300 to 3000 cells) were seeded on 60 mm plates and were incubated overnight to adhere. Next day, the cells were treated with increasing A-TPZ doses and the plates were exposed to both normoxic (20% $O_2$) and hypoxic (0.5% $O_2$) conditions for 24 hours. The media was changed and the plates were incubated for 14 days (at 37° C. with 5% $CO_2$) to let the colonies develop. Colonies were stained with crystal violet solution and counted. Error bars represent the standard error of the mean.

Hypoxia-Selective Sub-Cellular Localization

Click reaction, performed between A-TPZ and alexa-594 alkyne, showed selective sub-cellular localization of A-TPZ in cells exposed to hypoxia (<0.1 $O_2$) [FIG. 11]. It is evident that the drug shows more cytoskeletal staining with predominant nucleolar and nuclear localization. The signal intensity was observed to be dose-dependent [FIG. 22-B,C, D]. No fluorescence was seen in normoxic drug treated cells [FIG. 11-A], which confirms that A-TPZ, when reduced, binds to alkyne (Alexa-594) by click chemistry, specifically to hypoxic cells in situ. This, thereby confirms the selectivity of the compound. In general, it seems to be an effective approach to monitor the TPZ uptake.

FIG. 11 shows that A-TPZ Click chemistry demonstrates hypoxia-selective mapping potential, which is dose-dependent. FaDu cells were seeded on coverslips and were incubated overnight to adhere. The cells were then treated with increasing doses of A-TPZ for 24 hours under normoxic and hypoxic (<0.1% $O_2$) conditions. Cells were fixed in 2% paraformaldehyde and Click chemistry was performed at room temperature for 30 minutes using Alexa 594 alkyne. Nuclei were counterstained with Hoechst, and images were obtained using confocal microscopy.

REFERENCES

Hall E J. Radiobiology for the radiobiologist. Pub. J.B. Lippincott Co., Philadelphia, USA. (1994).

Bennewith K L, and S Dedhar. Targeting hypoxic tumor cells to overcome metastasis. BMC Cancer. 11:504 (2011).

Padera T P, B R Stoll, J B Tooredman, D Capen, E di Tomaso, R K Jain. Pathology: cancer cells compress intratumoral vessels. Nature. 427:695-695 (2004).

Intaglietta M, R R Myers, J F Gross, H S Reinhold. Dynamics of microvascular flow in implanted mouse mammary tumors. Bibl Anat. 15:273-276 (1977).

Chaplin D J, P L Olive, R E Durand. Intermittent blood flow in a murine tumor: Radiobiological effects. Cancer Res. 47:597-601 (1987).

Minchinton A I, I F Tannock. Drug penetration in solid tumors. Nature Rev. 6:583-592 (2006).

Jain R K. Delivery of molecular and cellular medicine to solid tumors. Microcirculation. 4:3-21 (1997).

Heidin C H, K Rubin, K Pietras, AOstman. High interstitial fluid pressure—an obstacle in cancer therapy. Nature Rev Cancer. 4:806-813 (2004).

Stratton M R. P J Campbell, P A Futreal. The cancer genome. Nature. 458:719-724 (2009).

Nordsmark M, M Overgaard, J Overgaard. Pretreatment oxygenation predicts radiation response in advanced squamous cell carcinoma of the head and neck. Radiother Oncol. 41:31-9, (1996).

Bindra R S, M E Crosby, P M Glazer, A L Harris. Regulation of DNA repair in hypoxic cancer cells. Cancer Metastasis. 26:249-260, (2007).

Bencokova Z, M R Kaufmann, I M Pires, P S Lecane, E M Hammond, ATM activation and signaling under hypoxic conditions. Mol Cell Biol. 29:526-537, (2009).

Lee N Y, Q T Le. New developments in radiation therapy for head and neck cancer: intensity-modulated radiation therapy and hypoxia targeting. Semin Oncol. 35:236-50 (2008).

Chi J T, Z Wang, D S Nuyten, E H Rodriguez, M E Schaner, A Salim, Y Wang, G B Kristensen, A Helland, A L Borrasen-Dale, A Giaccia, M T Longaker, T Hastie, G P Yang, M J van der Vijver, P O Brown. Gene expression programs in response to hypoxia: cell type specificity and prognostic significance in human cancers. PloS Med. 3: e47 (2006).

Ma H I, S H Chiou, D Y Hueng, L K Tai, P I Huang, C L Kao, Y W Chen, H K Sytwu. Celecoxib and radioresistant glioblastoma-derived CD133(+) cells: improvement in radiotherapeutic effects Laboratory investigation. J Neurosurgery. 114:651-662 (2011).

Keith B, M C Simon. Hypoxia-inducible factors, Stem cells and Cancer. Cell. 129:465-472 (2007).

Seidel S, B K Garvalov, V Wirta, L von Stechow, A Schanzer, K Meletis, M Wolter, D Sommerlad, A T Henze, M Nister, G Reifenberger, J Lundenberg, J Frisen, T Acker. A hypoxic niche regulates glioblastoma stem cells through hypoxia inducible factor 2alpha. Brain. 133:983-995 (2010).

Bar E E, A Lin, V Mahairaki, W Matsui, C G Eberhart. Hypoxia increases the expression of stem-cell markers and promotes clonogenicity in glioblastoma. Neurospheres. 1491-1502 (2010).

Birner P, M Piribauer, I Fischer, B Gatterbauer, C Marosi, P F Ambros, I M Ambeos, M Bredel, G Oberhuber, K Rossler, H Budka, AL Harris, J A Hainfellner. Vascular patterns in glioblastoma influence clinical outcome and associate with variable expression of angiogenic proteins: evidence for distinct angiogenic subtypes. Brain Pathol. 13:133-143 (2003).

Blazek E R, J L Foutch, G Maki G. Daoymedulloblastoma cells that express CD133 are radioresistant relative to CD133-cells, and the CD133+ sector is enlarged by hypoxia. Int J Radiat Oncol Biol Phys. 67:1-5 (2007).

Bristow R G, R P Hill. Hypoxia and metabolism: Hypoxia, DNA repair and genetic instability. Nat Rev Cancer. 8:180-92 (2008).

Clement V, V Dutoit, D Marino, P Y Dietrich, I Radovanovic. Limits of CD133 as a marker of glioma self-renewing cells. Int J Cancer. 125:244-248 (2009).

Brown J M. The hypoxic cell: a target for selective cancer therapy-eighteenth Bruce F. Cain memorial award lecture. Cancer Res. 59:5863-5870 (1999).

Kits

Method of the invention are conveniently practiced by providing the compounds and/or compositions used in such method in the form of a kit. Such kit preferably contains the compound(s) and/or composition(s).

As used herein, the term "instructions for administering said compound to a subject," and grammatical equivalents thereof, includes instructions for using the compositions contained in a kit for the treatment of conditions characterized by viral infection (e.g., providing dosing, route of administration, decision trees for treating physicians for correlating patient-specific characteristics with therapeutic courses of action). The compounds of the present invention (e.g. as shown in structures above and elsewhere presented herein) can be packaged into a kit, which may include instructions for administering the compounds to a subject.

It should be understood that the examples herein are for illustrative purposes only. Therefore, they should not limit the scope of this invention in anyway.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method of treating a cancer in a subject, comprising administering a compound with the structure of

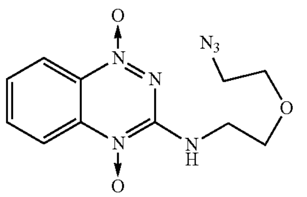

or

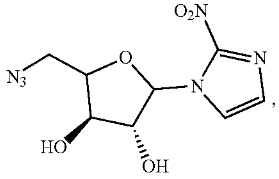

, or a radiolabeled compound thereof to the subject.

2. A method of imaging a cancer in a subject, comprising administering a compound with the structure of

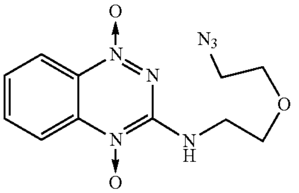

or

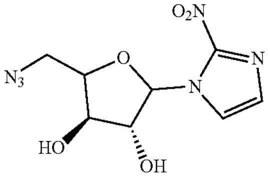

, or a radiolabeled compound thereof to the subject and detecting said compound or radiolabeled compound thereof.

3. A method of determining a level of hypoxia in a tissue, comprising administering to a subject a compound having the structure of

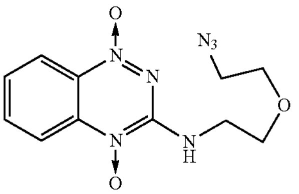

or

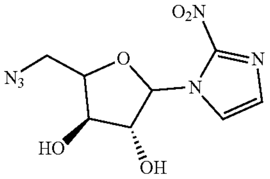

, wherein the compound comprises a fluorescent label or a radiolabel, and detecting an amount of said compound in the tissue.

4. The method of claim 3, wherein said detecting comprises fluorescence imaging, optical imaging, magnetic resonance imaging (MRI), radioactive positron emission tomography (PET), radioactive single-photon emission computed tomography (SPECT), or acoustic imaging.

5. A method of detecting hypoxia in cells, comprising administering to a subject a compound with the structure of

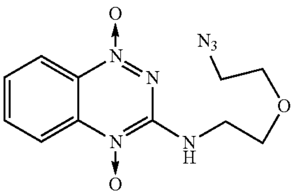

or

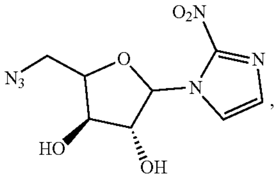

, wherein the compound comprises a fluorescent label or a radiolabel, and detecting the presence of the compound in hypoxic cells of the subject.

* * * * *